US006784305B2

(12) United States Patent
Schulte et al.

(10) Patent No.: US 6,784,305 B2
(45) Date of Patent: Aug. 31, 2004

(54) METHOD FOR PRODUCING ALKYL-BRIDGED LIGAND SYSTEMS AND TRANSITION METAL COMPOUNDS

(75) Inventors: Jörg Schulte, Frankfurt (DE); Carsten Bingel, Schifferstadt (DE); Jörg Schottek, Frankfurt (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 10/362,581

(22) PCT Filed: Aug. 22, 2001

(86) PCT No.: PCT/EP01/09682

§ 371 (c)(1),
(2), (4) Date: Feb. 25, 2003

(87) PCT Pub. No.: WO02/18397

PCT Pub. Date: Mar. 7, 2002

(65) Prior Publication Data

US 2003/0199703 A1 Oct. 23, 2003

(30) Foreign Application Priority Data

Aug. 29, 2000  (DE) ........................................ 100 424 50

(51) Int. Cl.$^7$ .............................. C07F 17/00; C07F 7/00; B01J 31/00
(52) U.S. Cl. ........................ 556/53; 502/103; 502/117; 526/160; 526/943
(58) Field of Search ............................ 556/53; 526/160, 526/943; 502/103, 117

(56) References Cited

U.S. PATENT DOCUMENTS

| 4,742,597 A | 5/1988 | Turner ........................ 502/104 |
| 5,017,714 A | 5/1991 | Welborn, Jr. .................. 556/12 |
| 6,051,522 A * | 4/2000 | Rohrmann et al. ......... 502/103 |

FOREIGN PATENT DOCUMENTS

| DE | 37 42 934 | 6/1989 |
| DE | 44 06 109 | 8/1995 |
| DE | 197 13549 | 10/1998 |
| DE | 199 62905 | 7/2001 |
| EP | 129 368 | 12/1984 |
| EP | 320 762 | 6/1989 |
| EP | 416 815 | 3/1991 |
| EP | 537 686 | 4/1993 |
| EP | 669 340 | 8/1995 |
| WO | 98/40331 | 9/1998 |

OTHER PUBLICATIONS

Brintzinger et al., Angew. Chem. Int., 1995, 34, 1143–1170.*
J.Org.Chem., 232 (1982) 233–247, Wild et al.
Chem.Ber.1994, 127,2417–2419, Rieger et al.
Organmetallics,1992,11,1869–1876, Reingold et al.
E.Linder, Chem.Ber.114, 810–813 (1981.

* cited by examiner

*Primary Examiner*—Porfirio Nazario-Gonzalez
(74) *Attorney, Agent, or Firm*—Keil & Weinkauf

(57) ABSTRACT

Highly substituted alkyl-bridged ligand systems based of indene derivatives and transition metal compounds can be obtained in high yields by a novel process.

6 Claims, No Drawings

METHOD FOR PRODUCING ALKYL-BRIDGED LIGAND SYSTEMS AND TRANSITION METAL COMPOUNDS

The present invention relates to a process for preparing alkyl-bridged ligand systems and transition metal compounds.

The preparation of metallocenes is known per se (U.S. Pat. No. 4,752,597; U.S. Pat. No. 5,017,714; EP-A-320762; EP-A-416815; EP-A-537686; EP-A-669340; H. H. Brintzinger et al.; Angew. Chem., 107 (1995), 1255; H. H. Brintzinger et al., J. Organomet. Chem. 232 (1982), 233). For this purpose, it is possible, for example, to react indenyl-metal compounds with halides of transition metals such as titanium, zirconium and hafnium.

Metallocenes can, possibly in combination with one or more cocatalysts, be used as catalyst components for the polymerization and copolymerization of olefins. In particular, halogen-containing metallocenes are used as catalyst precursors which can be converted into a polymerization-active cationic metallocene complex by means of, for example, an aluminoxane (EP-A-129368).

The polymerization properties of a metallocene compound can be controlled by means of the ligand system. Derivatives of zirconocene dichloride in which the two substituted indenyl groups are joined to one another via a bridge can, owing to their conformational rigidity, be used as catalysts for the stereospecific polymerization of olefins. Variation of this bridge enables the properties of the catalyst and the resulting polymer to be controlled in a targeted manner (Chemical Reviews 2000, Volume 100, Issue 4). Apart from dialkylsilanediyl-bridged metallocenes, ethylidene-bridged metallocenes are also known (DE 19713549).

Although a number of synthetic routes have been described for preparing simple carbon-bridged ligand systems bearing a few substituents, these cannot be applied to the preparation of highly substituted bisindenyl ligands.

A further difficulty in the synthesis of carbon-bridged, highly substituted metallocenes is the metallation of the ligand. The synthesis of these complexes is thus complicated and gives poor yields, which leads directly to increased costs and to limited commercial utility.

Chem. Ber. 1994, 127, 2417–2419, describes the synthesis of 1,2-bis(fluorenyl)-1-phenylethanezirconium dichloride. This unsubstituted alkyl-bridged metal complex is obtained in a yield of 13%.

Organometallics 1992, 11, 1869–1876, describes the synthesis of 2,3-butylene-1,1'-bis(indenyl)zirconium dichloride. This metal complex unsubstituted on the indenyl ligand is obtained in a yield of 18%.

It is an object of the present invention to find a new synthetic route to this class of compounds which avoids the disadvantages of the prior art described and gives the desired compounds in better yields.

We have found that this object is achieved by preparing the ligand systems from highly substituted indene derivatives and alternative bridging reagents, which gives good yields. The use of an alternative metal source leads to the target compounds in high yields and purities. The synthetic route described here gives a high total yield and high purities.

The present invention accordingly provides a process for preparing compounds of the formula I:

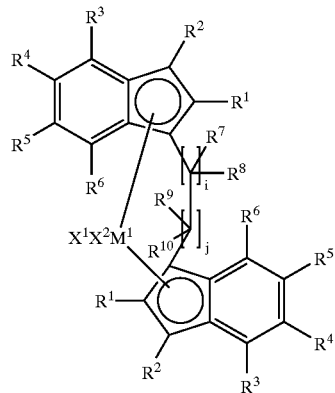

where
M$^1$ is Ti, Zr or Hf, particularly preferably zirconium,
R$^1$ are identical or different and are each hydrogen or a C$_1$–C$_{20}$ group, preferably C$_1$–C$_{18}$-alkyl, such as methyl, ethyl, n-propyl, n-butyl, n-pentyl, n-hexyl, n-heptyl, n-octyl, n-nonyl, n-decyl, cyclopentyl or cyclohexyl, isopropyl, isobutyl, isopentyl, isohexyl, tert-butyl, C$_2$–C$_{10}$-alkenyl, C$_3$–C$_{15}$-alkylalkenyl, C$_6$–C$_{18}$-aryl, C$_4$–C$_{18}$-heteroaryl, C$_7$–C$_{20}$-arylalkyl, C$_7$–C$_{20}$-alkylaryl, fluorinated C$_1$–C$_{12}$-alkyl, fluorinated C$_6$–C$_{18}$-aryl, fluorinated C$_7$–C$_{20}$-arylalkyl or fluorinated C$_7$–C$_{20}$-alkylaryl, and R$^2$ are identical or different and are each hydrogen or a C$_1$–C$_{20}$ group, preferably C$_1$–C$_{18}$-alkyl such as methyl, ethyl, n-propyl, n-butyl, n-pentyl, n-hexyl, n-heptyl, n-octyl, n-nonyl, n-decyl, cyclopentyl or cyclohexyl, isopropyl, isobutyl, isopentyl, isohexyl, tert-butyl, C$_2$–C$_{10}$-alkenyl, C$_3$–C$_{15}$-alkylalkenyl, C$_6$–C$_{18}$-aryl, C$_4$–C$_{18}$-heteroaryl, C$_7$–C$_{20}$-arylalkyl, C$_7$–C$_{20}$-alkylaryl, fluorinated C$_1$–C$_{12}$-alkyl, fluorinated C$_6$–C$_{18}$-aryl, fluorinated C$_7$–C$_{20}$-arylalkyl or fluorinated C$_7$–C$_{20}$-alkylaryl, where R$^1$ together with R$^2$ may also form a monocyclic or polycyclic ring system, and R$^3$ are identical or different and are each a hydrogen atom or a C$_6$–C$_{18}$-aryl group which may be substituted, in particular phenyl, 4-methylphenyl, 4-ethylphenyl, 4-propylphenyl, 4-isopropylphenyl, 4-tert-butylphenyl, 4-methoxyphenyl, 1-naphthyl, 9-anthracenyl, 3,5-di-tert-butylphenyl, 4-trifluoromethylphenyl, C$_5$–C$_{18}$-heteroaryl, C$_7$–C$_{20}$-arylalkyl, C$_7$–C$_{20}$-alkylaryl, fluorinated C$_6$–C$_{18}$-aryl, fluorinated C$_7$–C$_{20}$-arylalkyl or fluorinated C$_7$–C$_{20}$-alkylaryl and two radicals R$^3$ and R$^4$ may form a monocyclic or polycyclic ring system, particularly preferably 4,5-benzindenyl, R$^4$ are identical or different and are each either a hydrogen atom or together with R$^3$ form a monocyclic or polycyclic ring system, R$^5$, R$^6$ are identical or different and are each a hydrogen atom or a C$_1$–C$_{20}$ group, preferably C$_2$–C$_{10}$-alkenyl, C$_3$–C$_{15}$-alkylalkenyl, C$_6$–C$_{18}$-aryl, C$_4$–C$_{18}$-heteroaryl, C$_7$–C$_{20}$-arylalkyl, C$_7$–C$_{20}$-alkylaryl, fluorinated C$_1$–C$_{12}$-alkyl, fluorinated C$_6$–C$_{18}$-aryl, fluorinated C$_7$–C$_{20}$-arylalkyl or fluorinated C$_7$–C$_{20}$-alkylaryl, R$^7$, R$^8$, R$^9$, R$^{10}$ are identical or different and are each a hydrogen atom or a C$_1$–C$_{20}$ group, e.g. methyl, ethyl, n-propyl, n-butyl, n-pentyl, n-hexyl, n-heptyl, n-octyl, n-nonyl, n-decyl, cyclopentyl or cyclohexyl, isopropyl, isobutyl, isopentyl, isohexyl, tert-butyl, C$_2$–C$_{10}$-alkenyl, C$_3$–C$_{15}$-alkylalkenyl, C$_6$–C$_{18}$-aryl, C$_4$–C$_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, and may among one another form a monocyclic or bicyclic ring system, e.g. cis- or trans-cyclopentyl, cyclohexyl, cycloheptyl, cyclooctyl, cyclononyl, cyclodecyl, i is from 1 to 10, preferably from 1 to 8, very particularly preferably from 1 to 3, and j is from 1 to 10, preferably from 1 to 8, very particularly preferably from 1 to 3, and $X^1$, $X^2$ may be identical or different and are each a halogen atom, in particular chlorine, an alkyl group, in particular methyl, or a substituted or unsubstituted phenoxide. $X^1$ together with one or more radicals $X^1$ or $X^2$ may also form a monocyclic or polycyclic ring system.

Despite being indexed the same, the two indenyl radicals can be substituted differently, e.g. $R^3$ may be phenyl in the first indenyl radical and may be naphthyl in the second indenyl radical.

For this purpose, a compound of the formula II

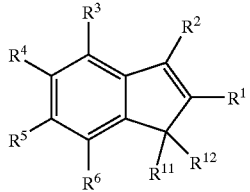

(II)

where $R^1$, $R^2$, $R^3$, $R^4$, $R^5$ and $R^6$ are as defined above and $R^{11}$ is a hydrogen atom and $R^{12}$ is a hydrogen atom or a group which can be replaced by a metal, preferably chlorine, bromine or iodine, is firstly reacted with a compound of the formula III $$M^2 R^{13}{}_n X^3{}_m \qquad (III)$$

where $M^2$ is an element of main group I or II of the Periodic Table of the Elements, preferably lithium, sodium, potassium or magnesium, particularly preferably lithium, and $R^{13}$ is a hydrogen atom or a $C_1$–$C_{20}$ group, preferably $C_1$–$C_{18}$-alkyl such as methyl, ethyl, n-butyl, n-hexyl, sec-butyl, tert-butyl, cyclohexyl or cyclooctyl, $C_2$–$C_{10}$-alkenyl, $C_3$–$C_{15}$-alkylalkenyl, $C_6$–$C_{18}$-aryl, such as phenyl, tolyl, xylyl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, preferably $C_1$–$C_{18}$-alkyl such as methyl, ethyl, n-butyl, n-hexyl, tert-butyl, $C_6$–$C_{18}$-aryl such as phenyl, tolyl, xylyl, particularly preferably methyl, ethyl, n-butyl, n-hexyl, tert-butyl, phenyl or tolyl, and $X^3$ is a halogen atom, preferably chlorine, bromine or iodine, and n is 1 or 2 and m is 0 or 1, in a solvent. The compounds of the formula III can be used in solution, as a pure substance or as a suspension or can be generated in situ from a metal $M^2$ such as lithium and an alkyl or aryl halide. Nonlimiting examples of preferred compounds of the formula III are:

methyllithium, ethyllithium, n-propyllithium, i-propyllithium, n-butyllithium, s-butyllithium, t-butyllithium, n-pentyllithium, s-pentyllithium, t-pentyllithium, n-hexyllithium, s-hexyllithium, t-hexyllithium, heptyllithium, octyllithium, nonyllithium, decyllithium, phenyllithium, o-tolyllithium, m-tolyllithium, p-tolyllithium, xylyllithium, methylsodium, ethylsodium, n-propylsodium, i-propylsodium, n-butylsodium, s-butylsodium, t-butylsodium, n-pentylsodium, s-pentylsodium, t-pentylsodium, n-hexylsodium, s-hexylsodium, t-hexylsodium, heptylsodium, octylsodium, nonylsodium, decylsodium, phenylsodium, o-tolylsodium, m-tolylsodium, p-tolylsodium, xylylsodium, methylpotassium, ethylpotassium, n-propylpotassium, i-propylpotassium, n-butylpotassium, s-butylpotassium, t-butylpotassium, n-pentylpotassium, s-pentylpotassium, t-pentylpotassium, n-hexylpotassium, s-hexylpotassium, t-hexylpotassium, heptylpotassium, octylpotassium, nonylpotassium, decylpotassium, phenylpotassium, o-tolylpotassium, m-tolylpotassium, p-tolylpotassium, xylylpotassium, methylmagnesium bromide, ethylmagnesium bromide, n-propylmagnesium bromide, i-propylmagnesium bromide, n-butylmagnesium bromide, s-butylmagnesium bromide, t-butylmagnesium bromide, n-pentylmagnesium bromide, s-pentylmagnesium bromide, t-pentylmagnesium bromide, n-hexylmagnesium bromide, s-hexylmagnesium bromide, t-hexylmagnesium bromide, heptylmagnesium bromide, octylmagnesium bromide, nonylmagnesium bromide, decylmagnesium bromide, phenylmagnesium bromide, o-tolylmagnesium bromide, m-tolylmagnesium bromide, p-tolylmagnesium bromide, xylylmagnesium bromide, dimethylmagnesium, diethylmagnesium, di-n-propylmagnesium, di-i-propylmagnesium, di-n-butylmagnesium, s-dibutylmagnesium, di-t-butylmagnesium, di-n-pentylmagnesium, s-dipentylmagnesium, di-t-pentylmagnesium, di-n-hexylmagnesium, s-dihexylmagnesium, di-t-hexylmagnesium, diheptylmagnesium, dioctylmagnesium, dinonylmagnesium, didecylmagnesium, diphenylmagnesium, o-ditolylmagnesium, m-ditolylmagnesium, p-ditolylmagnesium, butyloctylmagnesium and dixylylmagnesium.

One or more compounds of the formula II can first be placed in a reaction vessel. The compounds can either be dissolved or suspended in a solvent or be present as such. Suitable solvents are both polar aprotic solvents (cycloalkyl ethers, dialkyl ethers, alkyl aryl ethers, diaryl ethers) e.g. dimethyl ether, diethyl ether, dipropyl ether, diisopropyl ether, di-n-butyl ether, di-s-butyl ether, di-t-butyl ether, t-butyl methyl ether, dimethoxyethane, diethoxyethane, tetrahydrofuran, tetrahydropyran, anisole, diphenyl ether etc., and also nonpolar aprotic solvents (aliphatic or aromatic hydrocarbons), e.g. n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, etc., and mixtures of these. The compounds are initially charged at from −100° C. to 300° C., preferably from −78° C. to 100° C., particularly preferably at from −40° C. to 40° C. The compound of the formula II is preferably present in dissolved form or as a suspension. One or more compounds of the formula III can subsequently be added. These can likewise be dissolved or suspended in a solvent or can be used as such. Suitable solvents are those described above or mixtures thereof.

The addition can be carried out over a period of from 1 minute to up to 96 hours. Addition over a period of from 10 minutes to 8 hours is preferred. The temperature of the initial charge during the addition is from −100° C. to 200° C., preferably from −80° C. to 150° C., particularly preferably from −40° C. to 40° C. The temperature is selected so that at least one reactant is present in a liquid phase. The subsequent reaction temperature is preferably from −40° C. to 100° C. Furthermore, the reaction can be carried out at atmospheric pressure but can also be carried out at superatmospheric pressure, although this requires appropriate reactors. The stoichiometric ratio in which the compounds of the formulae II and III are combined is from 1:1000 to 1:0.011. Preference is given to a stoichiometric ratio of the compounds of the formulae II and III of from 1:100 to 1:11. Particular preference is given to a stoichiometric reaction based on the compounds of the formulae II and III. The reaction can be carried out either in the order described here or in the reverse order, i.e. by addition of compounds of the formula II in dissolved form, in suspension or as such to compounds of the formula III in dissolved form, in suspension or as such. In the latter case, the reaction conditions are analogous to those described here.

The reaction of a compound of the formula II with the compound of the formula III gives a compound of the formula IV

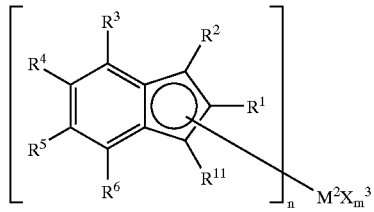

(IV)

where
$R^1$, $R^2$, $R^3$, $R^4$, $R^5$, $R^6$, $R^{11}$ are as defined above and
$M^2$ and $X^3$ are as defined above and
n is 1 or 2 and
m is 0 or 1.

Compounds of the formula IV can either be isolated or be reacted directly, in the same solvent or a different solvent, with a compound of the formula V

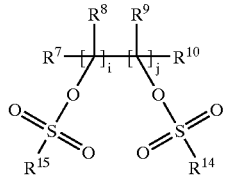

(V)

where
$R^7$, $R^8$, $R^9$ and $R^{10}$ are as defined above and
$R^{14}$, $R^{15}$ are identical or different and are each a $C_1$–$C_{20}$ group, e.g. $C_1$–$C_{18}$-alkyl such as methyl, ethyl, n-butyl, n-hexyl, sec-butyl, tert-butyl, cyclohexyl or cyclooctyl, $C_2$–$C_{10}$-alkenyl, $C_3$–$C_{15}$-alkylalkenyl, $C_6$–$C_{18}$-aryl such as phenyl, tolyl, xylyl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, preferably methyl, ethyl, propyl, i-propyl, n-butyl, s-butyl, t-butyl, pentyl etc., phenyl, tolyl, xylyl, trifluoromethyl, pentafluoroethyl, heptafluoropropyl, heptafluoroisopropyl etc., particularly preferably methyl, trifluoromethyl, p-tolyl, very particularly preferably trifluoromethyl, where $R^{14}$ and $R^{15}$ may also among one another form a nonhalogenated, partially halogenated or perhalogenated cyclic ring system and
i is from 1 to 10, preferably from 1 to 8, very particularly preferably from 1 to 3, and
j is from 1 to 10, preferably from 1 to 8, very particularly preferably from 1 to 3.

One or more compounds of the formula IV can firstly be placed in a reaction vessel.

The compounds can either be dissolved or suspended in a solvent or be present as such. Suitable solvents are both polar aprotic solvents (cycloalkyl ethers, dialkyl ethers, alkyl aryl ethers, diaryl ethers) e.g. dimethylformamide, dimethylacetamide, dimethyl sulfoxide, dimethyl ether, diethyl ether, dipropyl ether, diisopropyl ether, di-n-butyl ether, di-s-butyl ether, di-t-butyl ether, t-butyl methyl ether, dimethoxyethane, diethoxyethane, tetrahydrofuran, tetrahydropyran, anisole, diphenyl ether etc., and also nonpolar aprotic solvents (aliphatic or aromatic hydrocarbons), e.g. n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, etc., and mixtures of these. The compounds are initially charged at from −100° C. to 300° C., preferably from −78° C. to 100° C., particularly preferably at from −40° C. to 40° C. The compound of the formula IV is preferably present in dissolved form or as a suspension. One or more compounds of the formula V can subsequently be added. These can likewise be dissolved or suspended in a solvent or can be used as such. Suitable solvents are those described above or mixtures thereof.

The addition can be carried out over a period of from 1 minute to up to 96 hours. Addition over a period of from 10 minutes to 8 hours is preferred. The temperature of the initial charge during the addition is from −100° C. to 200° C., preferably from −80° C. to 150° C., particularly preferably from −40° C. to 40° C. The temperature is selected so that at least one reactant is present in a liquid phase. The subsequent reaction temperature is preferably from −40° C. to 100° C. Furthermore, the reaction can be carried out at atmospheric pressure but can also be carried out at superatmospheric pressure, although this requires appropriate reactors. The stoichiometric ratio in which the compounds of the formulae IV and V are combined is from 1:10 to 1:0.05. Preference is given to a stoichiometric ratio of the compounds of the formulae IV and V of from 1:2 to 1:0.25. Particular preference is given to a stoichiometric reaction based on the compounds of the formulae IV and V. The reaction can be carried out either in the order described here or in the reverse order, i.e. by addition of compounds of the formula IV in dissolved form, in suspension or as such to compounds of the formula V in dissolved form, in suspension or as such. In the latter case, the reaction conditions are analogous to those described here. The reaction mixture is worked up by hydrolysis and removal of water-soluble by-products. The product VI can either be purified by chromatography or recrystallization or can be reacted without further purification.

The reaction of a compound of the formula IV with a compound of the formula V gives a ligand system of the formula VI

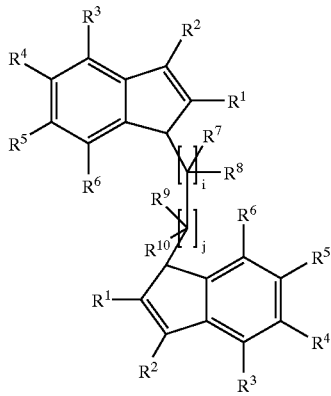
(VI)

where
$R^1, R^2, R^3, R^4, R^5, R^6, R^7, R^8, R^9, R^{10}$ are as defined above and
i and j are as defined above.

The compounds of the formula VI can be mixtures of various double bond isomers.

The transition metal complexes of the formula VII are synthesized by reacting a compound of the formula VI with a compound of the formula III. The compounds of the formula III can be used in solution, as such or as a suspension or can be generated in situ from a metal $M^2$, e.g. lithium, and an alkyl or aryl halide.

One or more compounds of the formula VI can first be placed in a reaction vessel. The compounds can either be dissolved or suspended in a solvent or be present as such. Suitable solvents are both polar aprotic solvents (cycloalkyl ethers, dialkyl ethers, alkyl aryl ethers, diaryl ethers) e.g. dimethyl ether, diethyl ether, dipropyl ether, diisopropyl ether, di-n-butyl ether, di-s-butyl ether, di-t-butyl ether, t-butyl methyl ether, dimethoxyethane, diethoxyethane, tetrahydrofuran, tetrahydropyran, anisole, diphenyl ether etc., and also nonpolar aprotic solvents (aliphatic or aromatic hydrocarbons), e.g. n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, etc., and mixtures of these. The compounds are initially charged at from −100° C. to 300° C., preferably from −78° C. to 100° C., particularly preferably at from −40° C. to 40° C. The compound of the formula II is preferably present in dissolved form or as a suspension. One or more compounds of the formula III can subsequently be added. These can likewise be dissolved or suspended in a solvent or can be used as such. Suitable solvents are those described above or mixtures thereof.

The addition can be carried out over a period of from 1 minute to up to 96 hours. Addition over a period of from 10 minutes to 8 hours is preferred. The temperature of the initial charge during the addition is from −100° C. to 200° C., preferably from −80° C. to 150° C., particularly preferably from −40° C. to 40° C. The temperature is selected so that at least one reactant is present in a liquid phase. The subsequent reaction temperature is preferably from −40° C. to 100° C. Furthermore, the reaction can be carried out at atmospheric pressure but can also be carried out at superatmospheric pressure, although this requires appropriate reactors. The stoichiometric ratio in which the compounds of the formulae VI and III are combined is from 1:10 to 1:1. Preference is given to a stoichiometric ratio of the compounds of the formulae VI and III of from 1:3 to 1:1.8. Particular preference is given to a stoichiometric ratio of the compounds of the formulae VI to the compounds of the formula III of from 1:2.2 to 1:2. The reaction can be carried out either in the order described here or in the reverse order, i.e. by addition of compounds of the formula VI in dissolved form, in suspension or as such to compounds of the formula III in dissolved form, in suspension or as such. In the latter case, the reaction conditions are analogous to those described here.

The reaction of a compound of the formula VI with a compound of the formula III gives a metallated ligand system of the formula VII

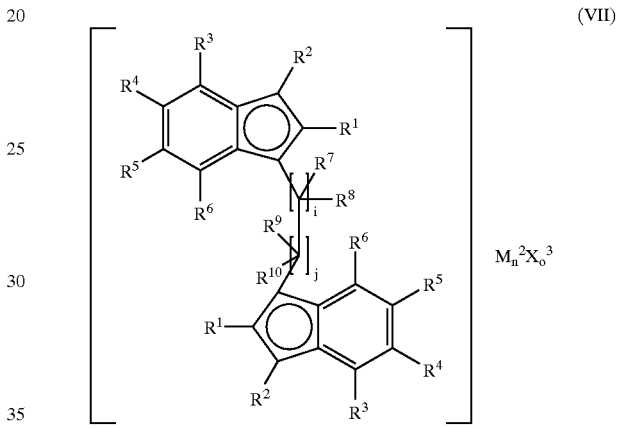
(VII)

where
$R^1, R^2, R^3, R^4, R^5, R^6, R^7, R^8, R^9, R^{10}$ and $R^{11}$ are as defined above and
$M^2$ and $X^3$ are as defined above and
n is 1 or 2 and
o is 0, 1 or 2 and
i and j are as defined above.

The compound of the formula VII can be isolated by a method analogous to that of DE 19739946 or prepared in situ and reacted with a compound of the formula VIII $$M^1(X^1)_f(X^2)_g(D)_a$$ (VIII)

where
$M^1$ is titanium, zirconium or hafnium, very particularly preferably zirconium, and
is a donor solvent containing at least one oxygen or sulfur atom, preferably 1 or 2 oxygen or sulfur atoms, very particularly preferably 1 or 2 oxygen atoms, and
$X^1$ and $X^2$ are identical or different and are as defined above, preferably halogen atoms or phenoxides, particularly preferably chlorine, bromine or iodine, very particularly preferably chlorine, and
f is from 0 to 4, preferably from 1 to 4, and
g is from 0 to 4, preferably from 1 to 4, and the sum f+g corresponds to the oxidation state of the metal ion,
a is from 1 to 100, preferably from 1 to 10, particularly preferably 1 or 2.
D is preferably an ether, cyclic ether or acetal, e.g. tetrahydrofuran, tetrahydropyran, diethyl ether, dimethoxymethane, diethoxymethane, dipropoxymethane, 1,2-dimethoxyethane, 1,2-diethoxyethane, 1,2-dipropoxyethane, 1,3-dimethoxypropane; 1,3-diethoxypropane, 1,3-dipropoxypropane, 1,2-dimethoxybenzene, 1,2-diethoxybenzene and/or 1,2-dipropoxybenzene.

$R_1$, $R^2$ are preferably identical and are each a $C_1$–$C_{20}$ group, preferably $C_1$–$C_{18}$-alkyl such as methyl, ethyl, n-propyl, n-butyl, n-pentyl, n-hexyl, n-heptyl, n-octyl, n-nonyl, n-decyl, cyclopentyl or cyclohexyl, isopropyl, isobutyl, isopentyl, isohexyl, tert-butyl, $C_2$–$C_{10}$-alkenyl, $C_3$–$C_{15}$-alkylalkenyl, $C_6$–$C_{18}$-aryl, $C_4$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, where $R^1$ together with $R^2$ may also form a monocyclic or polycyclic ring system.

Illustrative but nonlimiting examples of compounds of the formula VIII which can be prepared by the process of the present invention are:

$ZrCl_4$(tetrahydrofuran)$_2$; $ZrCl_4$(tetrahydropyran)2; $ZrCl_4$(diethyl ether)$_2$; $ZrCl_4$(dimethoxymethane); $ZrCl_4$(diethoxymethane);
$ZrCl_4$(dipropoxymethane); $ZrCl_4$(1,2-dimethoxyethane); $ZrCl_4$(1,2-diethoxyethane); $ZrCl_4$(1,2-dipropoxyethane);
$ZrCl_4$(1,3-dimethoxypropane); $ZrCl_4$(1,3-diethoxypropane);
$ZrCl_4$(1,3-dipropoxypropane); $ZrCl_4$(1,2-dimethoxybenzene);
$ZrCl_4$(1,2-diethoxybenzene); $ZrCl_4$(1,2-dipropoxybenzene);
$TiCl_4$(tetrahydrofuran)$_2$; $TiCl_4$(tetrahydropyran)$_2$; $TiCl_4$(diethyl ether)$_2$; $TiCl_4$(dimethoxymethane); $TiCl_4$(diethoxymethane);
$TiCl_4$(dipropoxymethane); $TiCl_4$(1,2-dimethoxyethane); $TiCl_4$(1,2-diethoxyethane); $TiCl_4$(1,2-dipropoxyethane);
$TiCl_4$(1,3-dimethoxypropane); $TiCl_4$(1,3-diethoxypropane);
$TiCl_4$(1,3-dipropoxypropane); $TiCl_4$(1,2-dimethoxybenzene);
$TiCl_4$(1,2-diethoxybenzene); $TiCl_4$(1,2-dipropoxybenzene);
$HfCl_4$(tetrahydrofuran)$_2$; $HfCl_4$(tetrahydropyran)$_2$; $HfCl_4$(diethyl ether)$_2$; $HfCl_4$(dimethoxymethane); $HfCl_4$(diethoxymethane);
$HfCl_4$(dipropoxymethane); $HfCl_4$(1,2-dimethoxyethane); $HfCl_4$(1,2-diethoxyethane); $HfCl_4$(1,2-dipropoxyethane);
$HfCl_4$(1,3-dimethoxypropane); $HfCl_4$(1,3-diethoxypropane);
$HfCl_4$(1,3-dipropoxypropane); $HfCl_4$(1,2-dimethoxybenzene);
$HfCl_4$(1,2-diethoxybenzene); $HfCl_4$(1,2-dipropoxybenzene).

To synthesize the transition metal complexes of the formula I, a compound of the formula VII is reacted with a compound of the formula VIII. The compounds of the formula VIII can be used in solution, as such or as a suspension or can be generated in situ from a metal halide of the formula $M^1X_fX_g$, e.g. zirconium tetrachloride, and a donor solvent $D_a$.

One or more compounds of the formula VII can first be placed in a reaction vessel. The compounds can either be dissolved or suspended in a solvent or be present as such. Suitable solvents are both polar aprotic solvents (cycloalkyl ethers, dialkyl ethers, alkyl aryl ethers, diaryl ethers) e.g. dimethyl ether, diethyl ether, dipropyl ether, diisopropyl ether, di-n-butyl ether, di-s-butyl ether, di-t-butyl ether, t-butyl methyl ether, dimethoxyethane, diethoxyethane, tetrahydrofuran, tetrahydropyran, anisole, diphenyl ether etc., and also nonpolar aprotic solvents (aliphatic or aromatic hydrocarbons), e.g. n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, etc., and mixtures of these. The compounds are initially charged at from −100° C. to 300° C., preferably from −78° C. to 100° C., particularly preferably at from −40° C. to 40° C. The compound of the formula VII is preferably present in dissolved form or as a suspension. One or more compounds of the formula VIII can subsequently be added. These can likewise be dissolved or suspended in a solvent or can be used as such. Suitable solvents are those described above or mixtures thereof.

The addition can be carried out over a period of from 1 minute to up to 96 hours. Addition over a period of from 10 minutes to 8 hours is preferred. The temperature of the initial charge during the addition is from −100° C. to 200° C., preferably from −80° C. to 150° C., particularly preferably from −40° C. to 40° C. The temperature is selected so that at least one reactant is present in a liquid phase. The subsequent reaction temperature is preferably from −40° C. to 100° C. Furthermore, the reaction can be carried out at atmospheric pressure but can also be carried out at superatmospheric pressure, although this requires appropriate reactors. The stoichiometric ratio in which the compounds of the formulae VII and VIII are combined is from 1:10 to 1:0.1. Preference is given to a stoichiometric ratio of the compounds of the formulae VII and VIII of from 1:5 to 1:0.5. Particular preference is given to a stoichiometric ratio of the compounds of the formula VII to the compounds of the formula VIII of 1:1. The reaction can be carried out either in the order described here or in the reverse order, i.e. by addition of compounds of the formula VII in dissolved form, in suspension or as such to compounds of the formula VIII in dissolved form, in suspension or as such. In the latter case, the reaction conditions are analogous to those described here.

The reaction of a compound of the formula VII with a compound of the formula VIII gives a transition metal compound of the formula I.

Preference is given to compounds of the formula I in which the respective radicals $R^1$ and also the respective radicals $R^3$ are identical.

Illustrative but nonlimiting examples of metallocenes which can be prepared by the synthetic route described here are:

1,2-ethanediylbis(2-methylindenyl)zirconium dichloride
1,2-ethanediylbis(2-methyl-4,5-benzindenyl)zirconium dichloride
1,2-ethanediylbis(2-methyl-4-phenylindenyl)zirconium dichloride
1,2-ethanediylbis(2-methyl-4-(4'-methylphenyl)indenyl) zirconium dichloride
1,2-ethanediylbis(2-methyl-4-(4'-ethylphenyl)indenyl) zirconium dichloride
1,2-ethanediylbis(2-methyl-4-(4'-propylphenyl)indenyl) zirconium dichloride
1,2-ethanediylbis(2-methyl-4-(4'-isopropylphenyl)indenyl) zirconium dichloride
1,2-ethanediylbis(2-methyl-4-(4'-tert-butylphenyl)indenyl) zirconium dichloride
1,2-ethanediylbis(2-methyl-4-(4'-methoxyphenyl)indenyl) zirconium dichloride
1,2-ethanediylbis(2-methyl-4-(1'-naphthyl)indenyl) zirconium dichloride
1,2-ethanediylbis(2-methyl-4-(9'-anthracenyl)indenyl) zirconium dichloride 1,2-ethanediylbis(2-methyl-4-(3',5'-di-tert-butylphenyl) indenyl)zirconium dichloride
1,2-ethanediylbis(2-methyl-4-(4'-trifluoromethylphenyl) indenyl)zirconium dichloride
1,2-ethanediylbis(9'-fluorenyl)zirconium dichloride
1,2-ethanediylbis(2-ethylindenyl)zirconium dichloride
1,2-ethanediylbis(2-ethyl-4,5-benzindenyl)zirconium dichloride
1,2-ethanediylbis(2-ethyl-4-phenylindenyl)zirconium dichloride
1,2-ethanediylbis(2-ethyl-4-(4'-methylphenyl)indenyl) zirconium dichloride
1,2-ethanediylbis(2-ethyl-4-(4'-ethylphenyl)indenyl) zirconium dichloride
1,2-ethanediylbis(2-ethyl-4-(4'-propylphenyl)indenyl) zirconium dichloride
1,2-ethanediylbis(2-ethyl-4-(4'-isopropylphenyl)indenyl) zirconium dichloride
1,2-ethanediylbis(2-ethyl-4-(4'-tert-butylphenyl)indenyl) zirconium dichloride
1,2-ethanediylbis(2-ethyl-4-(4'-methoxyphenyl)indenyl) zirconium dichloride
1,2-ethanediylbis(2-ethyl-4-(1'-naphthyl)indenyl)zirconium dichloride
1,2-ethanediylbis(2-ethyl-4-(9'-anthracenyl)indenyl) zirconium dichloride
1,2-ethanediylbis(2-ethyl-4-(3',5'-di-tert-butylphenyl) indenyl)zirconium dichloride
1,2-ethanediylbis(2-ethyl-4-(4'-trifluoromethylphenyl) indenyl)zirconium dichloride
1,2-ethanediylbis(2-propylindenyl)zirconium dichloride
1,2-ethanediylbis(2-propyl-4,5-benzindenyl)zirconium dichloride
1,2-ethanediylbis(2-propyl-4-phenylindenyl)zirconium dichloride
1,2-ethanediylbis(2-propyl-4-(4'-methylphenyl)indenyl) zirconium dichloride
1,2-ethanediylbis(2-propyl-4-(4'-ethylphenyl)indenyl) zirconium dichloride
1,2-ethanediylbis(2-propyl-4-(4'-propylphenyl)indenyl) zirconium dichloride
1,2-ethanediylbis(2-propyl-4-(4'-isopropylphenyl)indenyl) zirconium dichloride
1,2-ethanediylbis(2-propyl-4-(4'-tert-butylphenyl)indenyl) zirconium dichloride
1,2-ethanediylbis(2-propyl-4-(4'-methoxyphenyl)indenyl) zirconium dichloride
1,2-ethanediylbis(2-propyl-4-(1'-naphthyl)indenyl) zirconium dichloride
1,2-ethanediylbis(2-propyl-4-(9'-anthracenyl)indenyl) zirconium dichloride
1,2-ethanediylbis(2-propyl-4-(3',5'-di-tert-butylphenyl) indenyl)zirconium dichloride
1,2-ethanediylbis(2-propyl-4-(4'-trifluoromethylphenyl) indenyl)zirconium dichloride
1,2-ethanediylbis(2-isopropylindenyl)zirconium dichloride
1,2-ethanediylbis(2-isopropyl-4,5-benzindenyl)zirconium dichloride
1,2-ethanediylbis(2-isopropyl-4-phenylindenyl)zirconium dichloride
1,2-ethanediylbis(2-isopropyl-4-(4'-methylphenyl)indenyl) zirconium dichloride
1,2-ethanediylbis(2-isopropyl-4-(4'-ethylphenyl)indenyl) zirconium dichloride
1,2-ethanediylbis(2-isopropyl-4-(4'-propylphenyl)indenyl) zirconium dichloride
1,2-ethanediylbis(2-isopropyl-4-(4'-isopropylphenyl) indenyl) zirconium dichloride
1,2-ethanediylbis(2-isopropyl-4-(4'-tert-butylphenyl) indenyl)zirconium dichloride
1,2-ethanediylbis(2-isopropyl-4-(4'-methoxyphenyl) indenyl)zirconium dichloride
1,2-ethanediylbis(2-isopropyl-4-(1'-naphthyl)indenyl) zirconium dichloride
1,2-ethanediylbis(2-isopropyl-4-(9'-anthracenyl)indenyl) zirconium dichloride
1,2-ethanediylbis(2-isopropyl-4-(3',5'-di-tert-butylphenyl) indenyl)zirconium dichloride
1,2-ethanediylbis(2-isopropyl-4-(4'-trifluoromethylphenyl) indenyl)zirconium dichloride
1,2-ethanediylbis(2-isobutylindenyl)zirconium dichloride
1,2-ethanediylbis(2-isobutyl-4,5-benzindenyl)zirconium dichloride
1,2-ethanediylbis(2-isobutyl-4-phenylindenyl)zirconium dichloride
1,2-ethanediylbis(2-isobutyl-4-(4'-methylphenyl)indenyl) zirconium dichloride
1,2-ethanediylbis(2-isobutyl-4-(4'-ethylphenyl)indenyl) zirconium dichloride
1,2-ethanediylbis(2-isobutyl-4-(4'-propylphenyl)indenyl) zirconium dichloride
1,2-ethanediylbis(2-isobutyl-4-(4'-isopropylphenyl)indenyl) zirconium dichloride
1,2-ethanediylbis(2-isobutyl-4-(4'-tert-butylphenyl)indenyl) zirconium dichloride
1,2-ethanediylbis(2-isobutyl-4-(4'-methoxyphenyl)indenyl) zirconium dichloride
1,2-ethanediylbis(2-isobutyl-4-(1'-naphthyl)indenyl) zirconium dichloride
1,2-ethanediylbis(2-isobutyl-4-(9'-anthracenyl)indenyl) zirconium dichloride
1,2-ethanediylbis(2-isobutyl-4-(3',5'-di-tert-butylphenyl) indenyl)zirconium dichloride
1,2-ethanediylbis(2-isobutyl-4-(4'-trifluoromethylphenyl) indenyl)zirconium dichloride
1,2-ethanediylbis(2-butylindenyl)zirconium dichloride
1,2-ethanediylbis(2-butyl-4,5-benzindenyl)zirconium dichloride
1,2-ethanediylbis(2-butyl-4-phenylindenyl)zirconium dichloride
1,2-ethanediylbis(2-butyl-4-(4'-methylphenyl)indenyl) zirconium dichloride
1,2-ethanediylbis(2-butyl-4-(4'-ethylphenyl)indenyl) zirconium dichloride
1,2-ethanediylbis(2-butyl-4-(4'-propylphenyl)indenyl) zirconium dichloride
1,2-ethanediylbis(2-butyl-4-(4'-isopropylphenyl)indenyl) zirconium dichloride
1,2-ethanediylbis(2-butyl-4-(4'-tert-butylphenyl)indenyl) zirconium dichloride
1,2-ethanediylbis(2-butyl-4-(4'-methoxyphenyl)indenyl) zirconium dichloride
1,2-ethanediylbis(2-butyl-4-(1'-naphthyl)indenyl)zirconium dichloride
1,2-ethanediylbis(2-butyl-4-(9'-anthracenyl)indenyl) zirconium dichloride
1,2-ethanediylbis(2-butyl-4-(3',5'-di-tert-butylphenyl) indenyl)zirconium dichloride
1,2-ethanediylbis(2-butyl-4-(4'-trifluoromethylphenyl) indenyl) zirconium dichloride
1,2-ethanediylbis(2-tert-butylindenyl)zirconium dichloride
1,2-ethanediylbis(2-tert-butyl-4,5-benzindenyl)zirconium dichloride
1,2-ethanediylbis(2-tert-butyl-4-phenylindenyl)zirconium dichloride 1,2-ethanediylbis(2-tert-butyl-4-(4'-methylphenyl)indenyl)zirconium dichloride
1,2-ethanediylbis(2-tert-butyl-4-(4'-ethylphenyl)indenyl)zirconium dichloride
1,2-ethanediylbis(2-tert-butyl-4-(4'-propylphenyl)indenyl)zirconium dichloride
1,2-ethanediylbis(2-tert-butyl-4-(4'-isopropylphenyl)indenyl)zirconium dichloride
1,2-ethanediylbis(2-tert-butyl-4-(4'-tert-butylphenyl)indenyl)zirconium dichloride
1,2-ethanediylbis(2-tert-butyl-4-(4'-methoxyphenyl)indenyl)zirconium dichloride
1,2-ethanediylbis(2-tert-butyl-4-(1'-naphthyl)indenyl)zirconium dichloride
1,2-ethanediylbis(2-tert-butyl-4-(9'-anthracenyl)indenyl)zirconium dichloride
1,2-ethanediylbis(2-tert-butyl-4-(3',5'-di-tert-butylphenyl)indenyl)zirconium dichloride
1,2-ethanediylbis(2-tert-butyl-4-(4'-trifluoromethylphenyl)indenyl)zirconium dichloride
1,2-ethanediylbis(2-cyclopentylindenyl)zirconium dichloride
1,2-ethanediylbis(2-cyclopentyl-4,5-benzindenyl)zirconium dichloride
1,2-ethanediylbis(2-cyclopentyl-4-phenylindenyl)zirconium dichloride
1,2-ethanediylbis(2-cyclopentyl-4-(4'-methylphenyl)indenyl)zirconium dichloride
1,2-ethanediylbis(2-cyclopentyl-4-(4'-ethylphenyl)indenyl)zirconium dichloride
1,2-ethanediylbis(2-cyclopentyl-4-(4'-propylphenyl)indenyl)zirconium dichloride
1,2-ethanediylbis(2-cyclopentyl-4-(4'-isopropylphenyl)indenyl)zirconium dichloride
1,2-ethanediylbis(2-cyclopentyl-4-(4'-tert-butylphenyl)indenyl)zirconium dichloride
1,2-ethanediylbis(2-cyclopentyl-4-(4'-methoxyphenyl)indenyl)zirconium dichloride
1,2-ethanediylbis(2-cyclopentyl-4-(1'-naphthyl)indenyl)zirconium dichloride
1,2-ethanediylbis(2-cyclopentyl-4-(9'-anthracenyl)indenyl)zirconium dichloride
1,2-ethanediylbis(2-cyclopentyl-4-(3',5'-di-tert-butylphenyl)indenyl)zirconium dichloride
1,2-ethanediylbis(2-cyclopentyl-4-(4'-trifluoromethylphenyl)indenyl)zirconium dichloride
1,2-ethanediylbis(2-cyclohexylindenyl)zirconium dichloride
1,2-ethanediylbis(2-cyclohexyl-4,5-benzindenyl)zirconium dichloride
1,2-ethanediylbis(2-cyclohexyl-4-phenylindenyl)zirconium dichloride
1,2-ethanediylbis(2-cyclohexyl-4-(4'-methylphenyl)indenyl)zirconium dichloride
1,2-ethanediylbis(2-cyclohexyl-4-(4'-ethylphenyl)indenyl)zirconium dichloride
1,2-ethanediylbis(2-cyclohexyl-4-(4'-propylphenyl)indenyl)zirconium dichloride
1,2-ethanediylbis(2-cyclohexyl-4-(4'-isopropylphenyl)indenyl)zirconium dichloride
1,2-ethanediylbis(2-cyclohexyl-4-(4'-tert-butylphenyl)indenyl)zirconium dichloride
1,2-ethanediylbis(2-cyclohexyl-4-(4'-methoxyphenyl)indenyl)zirconium dichloride
1,2-ethanediylbis(2-cyclohexyl-4-(1'-naphthyl)indenyl)zirconium dichloride
1,2-ethanediylbis(2-cyclohexyl-4-(9'-anthracenyl)indenyl)zirconium dichloride
1,2-ethanediylbis(2-cyclohexyl-4-(3',5'-di-tert-butylphenyl)indenyl)zirconium dichloride
1,2-ethanediylbis(2-cyclohexyl-4-(4'-trifluoromethylphenyl)indenyl)zirconium dichloride
1,2-ethanediylbis(2-methylindenyl)titanium dichloride
1,2-ethanediylbis(2-methyl-4,5-benzindenyl)titanium dichloride
1,2-ethanediylbis(2-methyl-4-phenylindenyl)titanium dichloride
1,2-ethanediylbis(2-methyl-4-(4'-methylphenyl)indenyl)titanium dichloride
1,2-ethanediylbis(2-methyl-4-(4'-ethylphenyl)indenyl)titanium dichloride
1,2-ethanediylbis(2-methyl-4-(4'-propylphenyl)indenyl)titanium dichloride
1,2-ethanediylbis(2-methyl-4-(4'-isopropylphenyl)indenyl)titanium dichloride
1,2-ethanediylbis(2-methyl-4-(4'-tert-butylphenyl)indenyl)titanium dichloride
1,2-ethanediylbis(2-methyl-4-(4'-methoxyphenyl)indenyl)titanium dichloride
1,2-ethanediylbis(2-methyl-4-(1'-naphthyl)indenyl)titanium dichloride
1,2-ethanediylbis(2-methyl-4-(9'-anthracenyl)indenyl)titanium dichloride
1,2-ethanediylbis(2-methyl-4-(3',5'-di-tert-butylphenyl)indenyl)titanium dichloride
1,2-ethanediylbis(2-methyl-4-(4'-trifluoromethylphenyl)indenyl)titanium dichloride
1,2-ethanediylbis(9'-fluorenyl)titanium dichloride
1,2-ethanediylbis(2-ethylindenyl)titanium dichloride
1,2-ethanediylbis(2-ethyl-4,5-benzindenyl)titanium dichloride
1,2-ethanediylbis(2-ethyl-4-phenylindenyl)titanium dichloride
1,2-ethanediylbis(2-ethyl-4-(4'-methylphenyl)indenyl)titanium dichloride
1,2-ethanediylbis(2-ethyl-4-(4'-ethylphenyl)indenyl)titanium dichloride
1,2-ethanediylbis(2-ethyl-4-(4'-propylphenyl)indenyl)titanium dichloride
1,2-ethanediylbis(2-ethyl-4-(4'-isopropylphenyl)indenyl)titanium dichloride
1,2-ethanediylbis(2-ethyl-4-(4'-tert-butylphenyl)indenyl)titanium dichloride
1,2-ethanediylbis(2-ethyl-4-(4'-methoxyphenyl)indenyl)titanium dichloride
1,2-ethanediylbis(2-ethyl-4-(1'-naphthyl)indenyl)titanium dichloride
1,2-ethanediylbis(2-ethyl-4-(9'-anthracenyl)indenyl)titanium dichloride
1,2-ethanediylbis(2-ethyl-4-(3',5'-di-tert-butylphenyl)indenyl)titanium dichloride
1,2-ethanediylbis(2-ethyl-4-(4'-trifluoromethylphenyl)indenyl)titanium dichloride
1,2-ethanediylbis(2-propylindenyl)titanium dichloride
1,2-ethanediylbis(2-propyl-4,5-benzindenyl)titanium dichloride
1,2-ethanediylbis(2-propyl-4-phenylindenyl)titanium dichloride
1,2-ethanediylbis(2-propyl-4-(4'-methylphenyl)indenyl)titanium dichloride
1,2-ethanediylbis(2-propyl-4-(4'-ethylphenyl)indenyl)titanium dichloride
1,2-ethanediylbis(2-propyl-4-(4'-propylphenyl)indenyl)titanium dichloride
1,2-ethanediylbis(2-propyl-4-(4'-isopropylphenyl)indenyl)titanium dichloride 1,2-ethanediylbis(2-propyl-4-(4'-tert-butylphenyl)indenyl) titanium dichloride
1,2-ethanediylbis(2-propyl-4-(4'-methoxyphenyl)indenyl) titanium dichloride
1,2-ethanediylbis(2-propyl-4-(1'-naphthyl)indenyl)titanium dichloride
1,2-ethanediylbis(2-propyl-4-(9'-anthracenyl)indenyl) titanium dichloride
1,2-ethanediylbis(2-propyl-4-(3',5'-di-tert-butylphenyl) indenyl)titanium dichloride
1,2-ethanediylbis(2-propyl-4-(4'-trifluoromethylphenyl) indenyl)titanium dichloride
1,2-ethanediylbis(2-isopropylindenyl)titanium dichloride
1,2-ethanediylbis(2-isopropyl-4,5-benzindenyl)titanium dichloride
1,2-ethanediylbis(2-isopropyl-4-phenylindenyl)titanium dichloride
1,2-ethanediylbis(2-isopropyl-4-(4'-methylphenyl)indenyl) titanium dichloride
1,2-ethanediylbis(2-isopropyl-4-(4'-ethylphenyl)indenyl) titanium dichloride
1,2-ethanediylbis(2-isopropyl-4-(4'-propylphenyl)indenyl) titanium dichloride
1,2-ethanediylbis(2-isopropyl-4-(4'-isopropylphenyl) indenyl)titanium dichloride
1,2-ethanediylbis(2-isopropyl-4-(4'-tert-butylphenyl) indenyl)titanium dichloride
1,2-ethanediylbis(2-isopropyl-4-(4'-methoxyphenyl) indenyl)titanium dichloride
1,2-ethanediylbis(2-isopropyl-4-(1'-naphthyl)indenyl) titanium dichloride
1,2-ethanediylbis(2-isopropyl-4-(9'-anthracenyl)indenyl) titanium dichloride
1,2-ethanediylbis(2-isopropyl-4-(3',5'-di-tert-butylphenyl) indenyl)titanium dichloride
1,2-ethanediylbis(2-isopropyl-4-(4'-trifluoromethylphenyl) indenyl)titanium dichloride
1,2-ethanediylbis(2-isobutylindenyl)titanium dichloride
1,2-ethanediylbis(2-isobutyl-4,5-benzindenyl)titanium dichloride
1,2-ethanediylbis(2-isobutyl-4-phenylindenyl)titanium dichloride
1,2-ethanediylbis(2-isobutyl-4-(4'-methylphenyl)indenyl) titanium dichloride
1,2-ethanediylbis(2-isobutyl-4-(4'-ethylphenyl)indenyl) titanium dichloride
1,2-ethanediylbis(2-isobutyl-4-(4'-propylphenyl)indenyl) titanium dichloride
1,2-ethanediylbis(2-isobutyl-4-(4'-isopropylphenyl)indenyl) titanium dichloride
1,2-ethanediylbis(2-isobutyl-4-(4'-tert-butylphenyl)indenyl) titanium dichloride
1,2-ethanediylbis(2-isobutyl-4-(4'-methoxyphenyl)indenyl) titanium dichloride
1,2-ethanediylbis(2-isobutyl-4-(1'-naphthyl)indenyl) titanium dichloride
1,2-ethanediylbis(2-isobutyl-4-(9'-anthracenyl)indenyl) titanium dichloride
1,2-ethanediylbis(2-isobutyl-4-(3',5'-di-tert-butylphenyl) indenyl)titanium dichloride
1,2-ethanediylbis(2-isobutyl-4-(4'-trifluoromethylphenyl) indenyl)titanium dichloride
1,2-ethanediylbis(2-butylindenyl)titanium dichloride
1,2-ethanediylbis(2-butyl-4,5-benzindenyl)titanium dichloride
1,2-ethanediylbis(2-butyl-4-phenylindenyl)titanium dichloride
1,2-ethanediylbis(2-butyl-4-(4'-methylphenyl)indenyl) titanium dichloride
1,2-ethanediylbis(2-butyl-4-(4'-ethylphenyl)indenyl) titanium dichloride
1,2-ethanediylbis(2-butyl-4-(4'-propylphenyl)indenyl) titanium dichloride
1,2-ethanediylbis(2-butyl-4-(4'-isopropylphenyl)indenyl) titanium dichloride
1,2-ethanediylbis(2-butyl-4-(4'-tert-butylphenyl)indenyl) titanium dichloride
1,2-ethanediylbis(2-butyl-4-(4'-methoxyphenyl)indenyl) titanium dichloride
1,2-ethanediylbis(2-butyl-4-(1'-naphthyl)indenyl)titanium dichloride
1,2-ethanediylbis(2-butyl-4-(9'-anthracenyl)indenyl) titanium dichloride
1,2-ethanediylbis(2-butyl-4-(3',5'-di-tert-butylphenyl) indenyl)titanium dichloride
1,2-ethanediylbis(2-butyl-4-(4'-trifluoromethylphenyl) indenyl)titanium dichloride
1,2-ethanediylbis(2-tert-butylindenyl)titanium dichloride
1,2-ethanediylbis(2-tert-butyl-4,5-benzindenyl)titanium dichloride
1,2-ethanediylbis(2-tert-butyl-4-phenylindenyl)titanium dichloride
1,2-ethanediylbis(2-tert-butyl-4-(4'-methylphenyl)indenyl) titanium dichloride
1,2-ethanediylbis(2-tert-butyl-4-(4'-ethylphenyl)indenyl) titanium dichloride
1,2-ethanediylbis(2-tert-butyl-4-(4'-propylphenyl)indenyl) titanium dichloride
1,2-ethanediylbis(2-tert-butyl-4-(4'-isopropylphenyl) indenyl)titanium dichloride
1,2-ethanediylbis(2-tert-butyl-4-(4'-tert-butylphenyl) indenyl)titanium dichloride
1,2-ethanediylbis(2-tert-butyl-4-(4'-methoxyphenyl) indenyl)titanium dichloride
1,2-ethanediylbis(2-tert-butyl-4-(1'-naphthyl)indenyl) titanium dichloride
1,2-ethanediylbis(2-tert-butyl-4-(9'-anthracenyl)indenyl) titanium dichloride
1,2-ethanediylbis(2-tert-butyl-4-(3',5'-di-tert-butylphenyl) indenyl)titanium dichloride
1,2-ethanediylbis(2-tert-butyl-4-(4'-trifluoromethylphenyl) indenyl)titanium dichloride
1,2-ethanediylbis(2-cyclopentylindenyl)titanium dichloride
1,2-ethanediylbis(2-cyclopentyl-4,5-benzindenyl)titanium dichloride
1,2-ethanediylbis(2-cyclopentyl-4-phenylindenyl)titanium dichloride
1,2-ethanediylbis(2-cyclopentyl-4-(4'-methylphenyl) indenyl)titanium dichloride
1,2-ethanediylbis(2-cyclopentyl-4-(4'-ethylphenyl)indenyl) titanium dichloride
1,2-ethanediylbis(2-cyclopentyl-4-(4'-propylphenyl) indenyl)titanium dichloride
1,2-ethanediylbis(2-cyclopentyl-4-(4'-isopropylphenyl) indenyl)titanium dichloride
1,2-ethanediylbis(2-cyclopentyl-4-(4'-tert-butylphenyl) indenyl)titanium dichloride
1,2-ethanediylbis(2-cyclopentyl-4-(4'-methoxyphenyl) indenyl)titanium dichloride
1,2-ethanediylbis(2-cyclopentyl-4-(1'-naphthyl)indenyl) titanium dichloride
1,2-ethanediylbis(2-cyclopentyl-4-(9'-anthracenyl)indenyl) titanium dichloride
1,2-ethanediylbis(2-cyclopentyl-4-(3',5'-di-tert-butylphenyl)indenyl)titanium dichloride 1,2-ethanediylbis(2-cyclopentyl-4-(4'-trifluoromethylphenyl)indenyl)titanium dichloride
1,2-ethanediylbis(2-cyclohexylindenyl)titanium dichloride
1,2-ethanediylbis(2-cyclohexyl-4,5-benzindenyl)titanium dichloride
1,2-ethanediylbis(2-cyclohexyl-4-phenylindenyl)titanium dichloride
1,2-ethanediylbis(2-cyclohexyl-4-(4'-methylphenyl)indenyl)titanium dichloride
1,2-ethanediylbis(2-cyclohexyl-4-(4'-ethylphenyl)indenyl)titanium dichloride
1,2-ethanediylbis(2-cyclohexyl-4-(4'-propylphenyl)indenyl)titanium dichloride
1,2-ethanediylbis(2-cyclohexyl-4-(4'-isopropylphenyl)indenyl)titanium dichloride
1,2-ethanediylbis(2-cyclohexyl-4-(4'-tert-butylphenyl)indenyl)titanium dichloride
1,2-ethanediylbis(2-cyclohexyl-4-(4'-methoxyphenyl)indenyl)titanium dichloride
1,2-ethanediylbis(2-cyclohexyl-4-(1'-naphthyl)indenyl)titanium dichloride
1,2-ethanediylbis(2-cyclohexyl-4-(9'-anthracenyl)indenyl)titanium dichloride
1,2-ethanediylbis(2-cyclohexyl-4-(3',5'-di-tert-butylphenyl)indenyl)titanium dichloride
1,2-ethanediylbis(2-cyclohexyl-4-(4'-trifluoromethylphenyl)indenyl)titanium dichloride
1,2-ethanediylbis(2-methylindenyl)hafnium dichloride
1,2-ethanediylbis(2-methyl-4,5-benzindenyl)hafnium dichloride
1,2-ethanediylbis(2-methyl-4-phenylindenyl)hafnium dichloride
1,2-ethanediylbis(2-methyl-4-(4'-methylphenyl)indenyl)hafnium dichloride
1,2-ethanediylbis(2-methyl-4-(4'-ethylphenyl)indenyl)hafnium dichloride
1,2-ethanediylbis(2-methyl-4-(4'-propylphenyl)indenyl)hafnium dichloride
1,2-ethanediylbis(2-methyl-4-(4'-isopropylphenyl)indenyl)hafnium dichloride
1,2-ethanediylbis(2-methyl-4-(4'-tert-butylphenyl)indenyl)hafnium dichloride
1,2-ethanediylbis(2-methyl-4-(4'-methoxyphenyl)indenyl)hafnium dichloride
1,2-ethanediylbis(2-methyl-4-(1'-naphthyl)indenyl)hafnium dichloride
1,2-ethanediylbis(2-methyl-4-(9'-anthracenyl)indenyl)hafnium dichloride
1,2-ethanediylbis(2-methyl-4-(3',5'-di-tert-butylphenyl)indenyl)hafnium dichloride
1,2-ethanediylbis(2-methyl-4-(4'-trifluoromethylphenyl)indenyl)hafnium dichloride
1,2-ethanediylbis(9'-fluorenyl)hafnium dichloride
1,2-ethanediylbis(2-ethylindenyl)hafnium dichloride
1,2-ethanediylbis(2-ethyl-4,5-benzindenyl)hafnium dichloride
1,2-ethanediylbis(2-ethyl-4-phenylindenyl)hafnium dichloride
1,2-ethanediylbis(2-ethyl-4-(4'-methylphenyl)indenyl)hafnium dichloride
1,2-ethanediylbis(2-ethyl-4-(4'-ethylphenyl)indenyl)hafnium dichloride
1,2-ethanediylbis(2-ethyl-4-(4'-propylphenyl)indenyl)hafnium dichloride
1,2-ethanediylbis(2-ethyl-4-(4'-isopropylphenyl)indenyl)hafnium dichloride
1,2-ethanediylbis(2-ethyl-4-(4'-tert-butylphenyl)indenyl)hafnium dichloride
1,2-ethanediylbis(2-ethyl-4-(4'-methoxyphenyl)indenyl)hafnium dichloride
1,2-ethanediylbis(2-ethyl-4-(1'-naphthyl)indenyl)hafnium dichloride
1,2-ethanediylbis(2-ethyl-4-(9'-anthracenyl)indenyl)hafnium dichloride
1,2-ethanediylbis(2-ethyl-4-(3',5'-di-tert-butylphenyl)indenyl)hafnium dichloride
1,2-ethanediylbis(2-ethyl-4-(4'-trifluoromethylphenyl)indenyl)hafnium dichloride
1,2-ethanediylbis(2-propylindenyl)hafnium dichloride
1,2-ethanediylbis(2-propyl-4,5-benzindenyl)hafnium dichloride
1,2-ethanediylbis(2-propyl-4-phenylindenyl)hafnium dichloride
1,2-ethanediylbis(2-propyl-4-(4'-methylphenyl)indenyl)hafnium dichloride
1,2-ethanediylbis(2-propyl-4-(4'-ethylphenyl)indenyl)hafnium dichloride
1,2-ethanediylbis(2-propyl-4-(4'-propylphenyl)indenyl)hafnium dichloride
1,2-ethanediylbis(2-propyl-4-(4'-isopropylphenyl)indenyl)hafnium dichloride
1,2-ethanediylbis(2-propyl-4-(4'-tert-butylphenyl)indenyl)hafnium dichloride
1,2-ethanediylbis(2-propyl-4-(4'-methoxyphenyl)indenyl)hafnium dichloride
1,2-ethanediylbis(2-propyl-4-(1'-naphthyl)indenyl)hafnium dichloride
1,2-ethanediylbis(2-propyl-4-(9'-anthracenyl)indenyl)hafnium dichloride
1,2-ethanediylbis(2-propyl-4-(3',5'-di-tert-butylphenyl)indenyl)hafnium dichloride
1,2-ethanediylbis(2-propyl-4-(4'-trifluoromethylphenyl)indenyl)hafnium dichloride
1,2-ethanediylbis(2-isopropylindenyl)hafnium dichloride
1,2-ethanediylbis(2-isopropyl-4,5-benzindenyl)hafnium dichloride
1,2-ethanediylbis(2-isopropyl-4-phenylindenyl)hafnium dichloride
1,2-ethanediylbis(2-isopropyl-4-(4'-methylphenyl)indenyl)hafnium dichloride
1,2-ethanediylbis(2-isopropyl-4-(4'-ethylphenyl)indenyl)hafnium dichloride
1,2-ethanediylbis(2-isopropyl-4-(4'-propylphenyl)indenyl)hafnium dichloride
1,2-ethanediylbis(2-isopropyl-4-(4'-isopropylphenyl)indenyl)hafnium dichloride
1,2-ethanediylbis(2-isopropyl-4-(4'-tert-butylphenyl)indenyl)hafnium dichloride
1,2-ethanediylbis(2-isopropyl-4-(4'-methoxyphenyl)indenyl)hafnium dichloride
1,2-ethanediylbis(2-isopropyl-4-(1'-naphthyl)indenyl)hafnium dichloride
1,2-ethanediylbis(2-isopropyl-4-(9'-anthracenyl)indenyl)hafnium dichloride
1,2-ethanediylbis(2-isopropyl-4-(3',5'-di-tert-butylphenyl)indenyl)hafnium dichloride
1,2-ethanediylbis(2-isopropyl-4-(4'-trifluoromethylphenyl)indenyl)hafnium dichloride
1,2-ethanediylbis(2-isobutylindenyl)hafnium dichloride
1,2-ethanediylbis(2-isobutyl-4,5-benzindenyl)hafnium dichloride
1,2-ethanediylbis(2-isobutyl-4-phenylindenyl)hafnium dichloride
1,2-ethanediylbis(2-isobutyl-4-(4'-methylphenyl)indenyl)hafnium dichloride 1,2-ethanediylbis(2-isobutyl-4-(4'-ethylphenyl)indenyl) hafnium dichloride
1,2-ethanediylbis(2-isobutyl-4-(4'-propylphenyl)indenyl) hafnium dichloride
1,2-ethanediylbis(2-isobutyl-4-(4'-isopropylphenyl) hafnium dichloride
1,2-ethanediylbis(2-isobutyl-4-(4'-tert-butylphenyl)indenyl) hafnium dichloride
1,2-ethanediylbis(2-isobutyl-4-(4'-methoxyphenyl)indenyl) hafnium dichloride
1,2-ethanediylbis(2-isobutyl-4-(1'-naphthyl)indenyl) hafnium dichloride
1,2-ethanediylbis(2-isobutyl-4-(9'-anthracenyl)indenyl) hafnium dichloride
1,2-ethanediylbis(2-isobutyl-4-(3',5'-di-tert-butylphenyl) indenyl)hafnium dichloride
1,2-ethanediylbis(2-isobutyl-4-(4'-trifluoromethylphenyl) indenyl) hafnium dichloride
1,2-ethanediylbis(2-butylindenyl)hafnium dichloride
1,2-ethanediylbis(2-butyl-4,5-benzindenyl)hafnium dichloride
1,2-ethanediylbis(2-butyl-4-phenylindenyl)hafnium dichloride
1,2-ethanediylbis(2-butyl-4-(4'-methylphenyl)indenyl) hafnium dichloride
1,2-ethanediylbis(2-butyl-4-(4'-ethylphenyl)indenyl) hafnium dichloride
1,2-ethanediylbis(2-butyl-4-(4'-propylphenyl)indenyl) hafnium dichloride
1,2-ethanediylbis(2-butyl-4-(4'-isopropylphenyl)indenyl) hafnium dichloride
1,2-ethanediylbis(2-butyl-4-(4'-tert-butylphenyl)indenyl) hafnium dichloride
1,2-ethanediylbis(2-butyl-4-(4'-methoxyphenyl)indenyl) hafnium dichloride
1,2-ethanediylbis(2-butyl-4-(1'-naphthyl)indenyl)hafnium dichloride
1,2-ethanediylbis(2-butyl-4-(9'-anthracenyl)indenyl) hafnium dichloride
1,2-ethanediylbis(2-butyl-4-(3',5'-di-tert-butylphenyl) indenyl)hafnium dichloride
1,2-ethanediylbis(2-butyl-4-(4'-trifluoromethylphenyl) indenyl)hafnium dichloride
1,2-ethanediylbis(2-tert-butylindenyl)hafnium dichloride
1,2-ethanediylbis(2-tert-butyl-4,5-benzindenyl)hafnium dichloride
1,2-ethanediylbis(2-tert-butyl-4-phenylindenyl)hafnium dichloride
1,2-ethanediylbis(2-tert-butyl-4-(4'-methylphenyl)indenyl) hafnium dichloride
1,2-ethanediylbis(2-tert-butyl-4-(4'-ethylphenyl)indenyl) hafnium dichloride
1,2-ethanediylbis(2-tert-butyl-4-(4'-propylphenyl)indenyl) hafnium dichloride
1,2-ethanediylbis(2-tert-butyl-4-(4'-isopropylphenyl) indenyl)hafnium dichloride
1,2-ethanediylbis(2-tert-butyl-4-(4'-tert-butylphenyl) indenyl)hafnium dichloride
1,2-ethanediylbis(2-tert-butyl-4-(4'-methoxyphenyl) indenyl)hafnium dichloride
1,2-ethanediylbis(2-tert-butyl-4-(1'-naphthyl)indenyl) hafnium dichloride
1,2-ethanediylbis(2-tert-butyl-4-(9'-anthracenyl)indenyl) hafnium dichloride
1,2-ethanediylbis(2-tert-butyl-4-(3',5'-di-tert-butylphenyl) indenyl)hafnium dichloride
1,2-ethanediylbis(2-tert-butyl-4-(4'-trifluoromethylphenyl) indenyl)hafnium dichloride
1,2-ethanediylbis(2-cyclopentylindenyl)hafnium dichloride
1,2-ethanediylbis(2-cyclopentyl-4,5-benzindenyl)hafnium dichloride
1,2-ethanediylbis(2-cyclopentyl-4-phenylindenyl)hafnium dichloride
1,2-ethanediylbis(2-cyclopentyl-4-(4'-methylphenyl) indenyl)hafnium dichloride
1,2-ethanediylbis(2-cyclopentyl-4-(4'-ethylphenyl)indenyl) hafnium dichloride
1,2-ethanediylbis(2-cyclopentyl-4-(4'-propylphenyl) indenyl)hafnium dichloride
1,2-ethanediylbis(2-cyclopentyl-4-(4'-isopropylphenyl) indenyl)hafnium dichloride
1,2-ethanediylbis(2-cyclopentyl-4-(4'-tert-butylphenyl) indenyl)hafnium dichloride
1,2-ethanediylbis(2-cyclopentyl-4-(4'-methoxyphenyl) indenyl)hafnium dichloride
1,2-ethanediylbis(2-cyclopentyl-4-(1'-naphthyl)indenyl) hafnium dichloride
1,2-ethanediylbis(2-cyclopentyl-4-(9'-anthracenyl)indenyl) hafnium dichloride
1,2-ethanediylbis(2-cyclopentyl-4-(3',5'-di-tert-butylphenyl)indenyl)hafnium dichloride
1,2-ethanediylbis(2-cyclopentyl-4-(4'-trifluoromethylphenyl)indenyl)hafnium dichloride
1,2-ethanediylbis(2-cyclohexylindenyl)hafnium dichloride
1,2-ethanediylbis(2-cyclohexyl-4,5-benzindenyl)hafnium dichloride
1,2-ethanediylbis(2-cyclohexyl-4-phenylindenyl)hafnium dichloride
1,2-ethanediylbis(2-cyclohexyl-4-(4'-methylphenyl) indenyl)hafnium dichloride
1,2-ethanediylbis(2-cyclohexyl-4-(4'-ethylphenyl)indenyl) hafnium dichloride
1,2-ethanediylbis(2-cyclohexyl-4-(4'-propylphenyl)indenyl) hafnium dichloride
1,2-ethanediylbis(2-cyclohexyl-4-(4'-isopropylphenyl) indenyl)hafnium dichloride
1,2-ethanediylbis(2-cyclohexyl-4-(4'-tert-butylphenyl) indenyl)hafnium dichloride
1,2-ethanediylbis(2-cyclohexyl-4-(4'-methoxyphenyl) indenyl)hafnium dichloride
1,2-ethanediylbis(2-cyclohexyl-4-(1'-naphthyl)indenyl) hafnium dichloride
1,2-ethanediylbis(2-cyclohexyl-4-(9'-anthracenyl)indenyl) hafnium dichloride
1,2-ethanediylbis(2-cyclohexyl-4-(3',5'-di-tert-butylphenyl) indenyl)hafnium dichloride
1,2-ethanediylbis(2-cyclohexyl-4-(4'-trifluoromethylphenyl)indenyl)hafnium dichloride
1,2-cyclohexanediylbis(2-methylindenyl)zirconium dichloride
1,2-cyclohexanediylbis(2-methyl-4,5-benzindenyl) zirconium dichloride
1,2-cyclohexanediylbis(2-methyl-4-phenylindenyl) zirconium dichloride
1,2-cyclohexanediylbis(2-methyl-4-(4'-methylphenyl) indenyl)zirconium dichloride
1,2-cyclohexanediylbis(2-methyl-4-(4'-ethylphenyl) indenyl)zirconium dichloride
1,2-cyclohexanediylbis(2-methyl-4-(4'-propylphenyl) indenyl)zirconium dichloride
1,2-cyclohexanediylbis(2-methyl-4-(4'-isopropylphenyl) indenyl)zirconium dichloride
1,2-cyclohexanediylbis(2-methyl-4-(4'-tert-butylphenyl) indenyl)zirconium dichloride
1,2-cyclohexanediylbis(2-methyl-4-(4'-methoxyphenyl) indenyl)zirconium dichloride 1,2-cyclohexanediylbis(2-methyl-4-(1'-naphthyl)indenyl)
zirconium dichloride
1,2-cyclohexanediylbis(2-methyl-4-(9'-anthracenyl)
indenyl)zirconium dichloride
1,2-cyclohexanediylbis(2-methyl-4-(3',5'-di-tert-butylphenyl)indenyl)zirconium dichloride
1,2-cyclohexanediylbis(2-methyl-4-(4'-trifluoromethylphenyl)indenyl)zirconium dichloride
1,2-cyclohexanediylbis(2-ethylindenyl)zirconium dichloride
1,2-cyclohexanediylbis(2-ethyl-4,5-benzindenyl)zirconium dichloride
1,2-cyclohexanediylbis(2-ethyl-4-phenylindenyl)zirconium dichloride
1,2-cyclohexanediylbis(2-ethyl-4-(4'-methylphenyl)indenyl)zirconium dichloride
1,2-cyclohexanediylbis(2-ethyl-4-(4'-ethylphenyl)indenyl)zirconium dichloride
1,2-cyclohexanediylbis(2-ethyl-4-(4'-propylphenyl)indenyl)zirconium dichloride
1,2-cyclohexanediylbis(2-ethyl-4-(4'-isopropylphenyl)indenyl)zirconium dichloride
1,2-cyclohexanediylbis(2-ethyl-4-(4'-tert-butylphenyl)indenyl)zirconium dichloride
1,2-cyclohexanediylbis(2-ethyl-4-(4'-methoxyphenyl)indenyl)zirconium dichloride
1,2-cyclohexanediylbis(2-ethyl-4-(1'-naphthyl)indenyl)zirconium dichloride
1,2-cyclohexanediylbis(2-ethyl-4-(9'-anthracenyl)indenyl)zirconium dichloride
1,2-cyclohexanediylbis(2-ethyl-4-(3',5'-di-tert-butylphenyl)indenyl)zirconium dichloride
1,2-cyclohexanediylbis(2-ethyl-4-(4'-trifluoromethylphenyl)indenyl)zirconium dichloride
1,2-cyclohexanediylbis(2-propylindenyl)zirconium dichloride
1,2-cyclohexanediylbis(2-propyl-4,5-benzindenyl)zirconium dichloride
1,2-cyclohexanediylbis(2-propyl-4-phenylindenyl)zirconium dichloride
1,2-cyclohexanediylbis(2-propyl-4-(4'-methylphenyl)indenyl)zirconium dichloride
1,2-cyclohexanediylbis(2-propyl-4-(4'-ethylphenyl)indenyl)zirconium dichloride
1,2-cyclohexanediylbis(2-propyl-4-(4'-propylphenyl)indenyl)zirconium dichloride
1,2-cyclohexanediylbis(2-propyl-4-(4'-isopropylphenyl)indenyl)zirconium dichloride
1,2-cyclohexanediylbis(2-propyl-4-(4'-tert-butylphenyl)indenyl)zirconium dichloride
1,2-cyclohexanediylbis(2-propyl-4-(4'-methoxyphenyl)indenyl)zirconium dichloride
1,2-cyclohexanediylbis(2-propyl-4-(1'-naphthyl)indenyl)zirconium dichloride
1,2-cyclohexanediylbis(2-propyl-4-(9'-anthracenyl)indenyl)zirconium dichloride
1,2-cyclohexanediylbis(2-propyl-4-(3',5'-di-tert-butylphenyl)indenyl)zirconium dichloride
1,2-cyclohexanediylbis(2-propyl-4-(4'-trifluoromethylphenyl)indenyl)zirconium dichloride
1,2-cyclohexanediylbis(2-isopropylindenyl)zirconium dichloride
1,2-cyclohexanediylbis(2-isopropyl-4,5-benzindenyl)zirconium dichloride
1,2-cyclohexanediylbis(2-isopropyl-4-phenylindenyl)zirconium dichloride
1,2-cyclohexanediylbis(2-isopropyl-4-(4'-methylphenyl)indenyl)zirconium dichloride
1,2-cyclohexanediylbis(2-isopropyl-4-(4'-ethylphenyl)indenyl)zirconium dichloride
1,2-cyclohexanediylbis(2-isopropyl-4-(4'-propylphenyl)indenyl)zirconium dichloride
1,2-cyclohexanediylbis(2-isopropyl-4-(4'-isopropylphenyl)indenyl)zirconium dichloride
1,2-cyclohexanediylbis(2-isopropyl-4-(4'-tert-butylphenyl)indenyl)zirconium dichloride
1,2-cyclohexanediylbis(2-isopropyl-4-(4'-methoxyphenyl)indenyl)zirconium dichloride
1,2-cyclohexanediylbis(2-isopropyl-4-(1'-naphthyl)indenyl)zirconium dichloride
1,2-cyclohexanediylbis(2-isopropyl-4-(9'-anthracenyl)indenyl)zirconium dichloride
1,2-cyclohexanediylbis(2-isopropyl-4-(3',5'-di-tert-butylphenyl)indenyl)zirconium dichloride
1,2-cyclohexanediylbis(2-isopropyl-4-(4'-trifluoromethylphenyl)indenyl)zirconium dichloride
1,2-cyclohexanediylbis(2-isobutylindenyl)zirconium dichloride
1,2-cyclohexanediylbis(2-isobutyl-4,5-benzindenyl)zirconium dichloride
1,2-cyclohexanediylbis(2-isobutyl-4-phenylindenyl)zirconium dichloride
1,2-cyclohexanediylbis(2-isobutyl-4-(4'-methylphenyl)indenyl)zirconium dichloride
1,2-cyclohexanediylbis(2-isobutyl-4-(4'-ethylphenyl)indenyl)zirconium dichloride
1,2-cyclohexanediylbis(2-isobutyl-4-(4'-propylphenyl)indenyl)zirconium dichloride
1,2-cyclohexanediylbis(2-isobutyl-4-(4'-isopropylphenyl)indenyl)zirconium dichloride
1,2-cyclohexanediylbis(2-isobutyl-4-(4'-tert-butylphenyl)indenyl)zirconium dichloride
1,2-cyclohexanediylbis(2-isobutyl-4-(4'-methoxyphenyl)indenyl)zirconium dichloride
1,2-cyclohexanediylbis(2-isobutyl-4-(1'-naphthyl)indenyl)zirconium dichloride
1,2-cyclohexanediylbis(2-isobutyl-4-(9'-anthracenyl)indenyl)zirconium dichloride
1,2-cyclohexanediylbis(2-isobutyl-4-(3',5'-di-tert-butylphenyl)indenyl)zirconium dichloride
1,2-cyclohexanediylbis(2-isobutyl-4-(4'-trifluoromethylphenyl)indenyl)zirconium dichloride
1,2-cyclohexanediylbis(2-butylindenyl)zirconium dichloride
1,2-cyclohexanediylbis(2-butyl-4,5-benzindenyl)zirconium dichloride
1,2-cyclohexanediylbis(2-butyl-4-phenylindenyl)zirconium dichloride
1,2-cyclohexanediylbis(2-butyl-4-(4'-methylphenyl)indenyl)zirconium dichloride
1,2-cyclohexanediylbis(2-butyl-4-(4'-ethylphenyl)indenyl)zirconium dichloride
1,2-cyclohexanediylbis(2-butyl-4-(4'-propylphenyl)indenyl)zirconium dichloride
1,2-cyclohexanediylbis(2-butyl-4-(4'-isopropylphenyl)indenyl)zirconium dichloride
1,2-cyclohexanediylbis(2-butyl-4-(4'-tert-butylphenyl)indenyl)zirconium dichloride
1,2-cyclohexanediylbis(2-butyl-4-(4'-methoxyphenyl)indenyl)zirconium dichloride
1,2-cyclohexanediylbis(2-butyl-4-(1'-naphthyl)indenyl)zirconium dichloride
1,2-cyclohexanediylbis(2-butyl-4-(9'-anthracenyl)indenyl)zirconium dichloride
1,2-cyclohexanediylbis(2-butyl-4-(3',5'-di-tert-butylphenyl)indenyl)zirconium dichloride 1,2-cyclohexanediylbis(2-butyl-4-(4'-trifluoromethylphenyl)indenyl)zirconium dichloride
1,2-cyclohexanediylbis(2-tert-butylindenyl)zirconium dichloride
1,2-cyclohexanediylbis(2-tert-butyl-4,5-benzindenyl)zirconium dichloride
1,2-cyclohexanediylbis(2-tert-butyl-4-phenylindenyl)zirconium dichloride
1,2-cyclohexanediylbis(2-tert-butyl-4-(4'-methylphenyl)indenyl)zirconium dichloride
1,2-cyclohexanediylbis(2-tert-butyl-4-(4'-ethylphenyl)indenyl)zirconium dichloride
1,2-cyclohexanediylbis(2-tert-butyl-4-(4'-propylphenyl)indenyl)zirconium dichloride
1,2-cyclohexanediylbis(2-tert-butyl-4-(4'-isopropylphenyl)indenyl)zirconium dichloride
1,2-cyclohexanediylbis(2-tert-butyl-4-(4'-tert-butylphenyl)indenyl)zirconium dichloride
1,2-cyclohexanediylbis(2-tert-butyl-4-(4'-methoxyphenyl)indenyl)zirconium dichloride
1,2-cyclohexanediylbis(2-tert-butyl-4-(1'-naphthyl)indenyl)zirconium dichloride
1,2-cyclohexanediylbis(2-tert-butyl-4-(9'-anthracenyl)indenyl)zirconium dichloride
1,2-cyclohexanediylbis(2-tert-butyl-4-(3',5'-di-tert-butylphenyl)indenyl)zirconium dichloride
1,2-cyclohexanediylbis(2-tert-butyl-4-(4'-trifluoromethylphenyl)indenyl)zirconium dichloride
1,2-cyclohexanediylbis(2-cyclopentylindenyl)zirconium dichloride
1,2-cyclohexanediylbis(2-cyclopentyl-4,5-benzindenyl)zirconium dichloride
1,2-cyclohexanediylbis(2-cyclopentyl-4-phenylindenyl)zirconium dichloride
1,2-cyclohexanediylbis(2-cyclopentyl-4-(4'-methylphenyl)indenyl)zirconium dichloride
1,2-cyclohexanediylbis(2-cyclopentyl-4-(4'-ethylphenyl)indenyl)zirconium dichloride
1,2-cyclohexanediylbis(2-cyclopentyl-4-(4'-propylphenyl)indenyl)zirconium dichloride
1,2-cyclohexanediylbis(2-cyclopentyl-4-(4'-isopropylphenyl)indenyl)zirconium dichloride
1,2-cyclohexanediylbis(2-cyclopentyl-4-(4'-tert-butylphenyl)indenyl)zirconium dichloride
1,2-cyclohexanediylbis(2-cyclopentyl-4-(4'-methoxyphenyl)indenyl)zirconium dichloride
1,2-cyclohexanediylbis(2-cyclopentyl-4-(1'-naphthyl)indenyl)zirconium dichloride
1,2-cyclohexanediylbis(2-cyclopentyl-4-(9'-anthracenyl)indenyl)zirconium dichloride
1,2-cyclohexanediylbis(2-cyclopentyl-4-(3',5'-di-tert-butylphenyl)indenyl)zirconium dichloride
1,2-cyclohexanediylbis(2-cyclopentyl-4-(4'-trifluoromethylphenyl)indenyl)zirconium dichloride
1,2-cyclohexanediylbis(2-cyclohexylindenyl)zirconium dichloride
1,2-cyclohexanediylbis(2-cyclohexyl-4,5-benzindenyl)zirconium dichloride
1,2-cyclohexanediylbis(2-cyclohexyl-4-phenylindenyl)zirconium dichloride
1,2-cyclohexanediylbis(2-cyclohexyl-4-(4'-methylphenyl)indenyl)zirconium dichloride
1,2-cyclohexanediylbis(2-cyclohexyl-4-(4'-ethylphenyl)indenyl)zirconium dichloride
1,2-cyclohexanediylbis(2-cyclohexyl-4-(4'-propylphenyl)indenyl)zirconium dichloride
1,2-cyclohexanediylbis(2-cyclohexyl-4-(4'-isopropylphenyl)indenyl)zirconium dichloride
1,2-cyclohexanediylbis(2-cyclohexyl-4-(4'-tert-butylphenyl)indenyl)zirconium dichloride
1,2-cyclohexanediylbis(2-cyclohexyl-4-(4'-methoxyphenyl)indenyl)zirconium dichloride
1,2-cyclohexanediylbis(2-cyclohexyl-4-(1'-naphthyl)indenyl)zirconium dichloride
1,2-cyclohexanediylbis(2-cyclohexyl-4-(9'-anthracenyl)indenyl)zirconium dichloride
1,2-cyclohexanediylbis(2-cyclohexyl-4-(3',5'-di-tert-butylphenyl)indenyl)zirconium dichloride
1,2-cyclohexanediylbis(2-cyclohexyl-4-(4'-trifluoromethylphenyl)indenyl)zirconium dichloride
1,2-cyclohexanediylbis(2-methylindenyl)titanium dichloride
1,2-cyclohexanediylbis(2-methyl-4,5-benzindenyl)titanium dichloride
1,2-cyclohexanediylbis(2-methyl-4-phenylindenyl)titanium dichloride
1,2-cyclohexanediylbis(2-methyl-4-(4'-methylphenyl)indenyl)titanium dichloride
1,2-cyclohexanediylbis(2-methyl-4-(4'-ethylphenyl)indenyl)titanium dichloride
1,2-cyclohexanediylbis(2-methyl-4-(4'-propylphenyl)indenyl)titanium dichloride
1,2-cyclohexanediylbis(2-methyl-4-(4'-isopropylphenyl)indenyl)titanium dichloride
1,2-cyclohexanediylbis(2-methyl-4-(4'-tert-butylphenyl)indenyl)titanium dichloride
1,2-cyclohexanediylbis(2-methyl-4-(4'-methoxyphenyl)indenyl)titanium dichloride
1,2-cyclohexanediylbis(2-methyl-4-(1'-naphthyl)indenyl)titanium dichloride
1,2-cyclohexanediylbis(2-methyl-4-(9'-anthracenyl)indenyl)titanium dichloride
1,2-cyclohexanediylbis(2-methyl-4-(3',5'-di-tert-butylphenyl)indenyl)titanium dichloride
1,2-cyclohexanediylbis(2-methyl-4-(4'-trifluoromethylphenyl)indenyl)titanium dichloride
1,2-cyclohexanediylbis(2-ethylindenyl)titanium dichloride
1,2-cyclohexanediylbis(2-ethyl-4,5-benzindenyl)titanium dichloride
1,2-cyclohexanediylbis(2-ethyl-4-phenylindenyl)titanium dichloride
1,2-cyclohexanediylbis(2-ethyl-4-(4'-methylphenyl)indenyl)titanium dichloride
1,2-cyclohexanediylbis(2-ethyl-4-(4'-ethylphenyl)indenyl)titanium dichloride
1,2-cyclohexanediylbis(2-ethyl-4-(4'-propylphenyl)indenyl)titanium dichloride
1,2-cyclohexanediylbis(2-ethyl-4-(4'-isopropylphenyl)indenyl)titanium dichloride
1,2-cyclohexanediylbis(2-ethyl-4-(4'-tert-butylphenyl)indenyl)titanium dichloride
1,2-cyclohexanediylbis(2-ethyl-4-(4'-methoxyphenyl)indenyl)titanium dichloride
1,2-cyclohexanediylbis(2-ethyl-4-(1'-naphthyl)indenyl)titanium dichloride
1,2-cyclohexanediylbis(2-ethyl-4-(9'-anthracenyl)indenyl)titanium dichloride
1,2-cyclohexanediylbis(2-ethyl-4-(3',5'-di-tert-butylphenyl)indenyl)titanium dichloride
1,2-cyclohexanediylbis(2-ethyl-4-(4'-trifluoromethylphenyl)indenyl)titanium dichloride
1,2-cyclohexanediylbis(2-propylindenyl)titanium dichloride
1,2-cyclohexanediylbis(2-propyl-4,5-benzindenyl)titanium dichloride
1,2-cyclohexanediylbis(2-propyl-4-phenylindenyl)titanium dichloride 1,2-cyclohexanediylbis(2-propyl-4-(4'-methylphenyl)indenyl)titanium dichloride
1,2-cyclohexanediylbis(2-propyl-4-(4'-ethylphenyl)indenyl)titanium dichloride
1,2-cyclohexanediylbis(2-propyl-4-(4'-propylphenyl)indenyl)titanium dichloride
1,2-cyclohexanediylbis(2-propyl-4-(4'-isopropylphenyl)indenyl)titanium dichloride
1,2-cyclohexanediylbis(2-propyl-4-(4'-tert-butylphenyl)indenyl)titanium dichloride
1,2-cyclohexanediylbis(2-propyl-4-(4'-methoxyphenyl)indenyl)titanium dichloride
1,2-cyclohexanediylbis(2-propyl-4-(1'-naphthyl)indenyl)titanium dichloride
1,2-cyclohexanediylbis(2-propyl-4-(9'-anthracenyl)indenyl)titanium dichloride
1,2-cyclohexanediylbis(2-propyl-4-(3',5'-di-tert-butylphenyl)indenyl)titanium dichloride
1,2-cyclohexanediylbis(2-propyl-4-(4'-trifluoromethylphenyl)indenyl)titanium dichloride
1,2-cyclohexanediylbis(2-isopropylindenyl)titanium dichloride
1,2-cyclohexanediylbis(2-isopropyl-4,5-benzindenyl)titanium dichloride
1,2-cyclohexanediylbis(2-isopropyl-4-phenylindenyl)titanium dichloride
1,2-cyclohexanediylbis(2-isopropyl-4-(4'-methylphenyl)indenyl)titanium dichloride
1,2-cyclohexanediylbis(2-isopropyl-4-(4'-ethylphenyl)indenyl)titanium dichloride
1,2-cyclohexanediylbis(2-isopropyl-4-(4'-propylphenyl)indenyl)titanium dichloride
1,2-cyclohexanediylbis(2-isopropyl-4-(4'-isopropylphenyl)indenyl)titanium dichloride
1,2-cyclohexanediylbis(2-isopropyl-4-(4'-tert-butylphenyl)indenyl)titanium dichloride
1,2-cyclohexanediylbis(2-isopropyl-4-(4'-methoxyphenyl)indenyl)titanium dichloride
1,2-cyclohexanediylbis(2-isopropyl-4-(1'-naphthyl)indenyl)titanium dichloride
1,2-cyclohexanediylbis(2-isopropyl-4-(9'-anthracenyl)indenyl)titanium dichloride
1,2-cyclohexanediylbis(2-isopropyl-4-(3',5'-di-tert-butylphenyl)indenyl)titanium dichloride
1,2-cyclohexanediylbis(2-isopropyl-4-(4'-trifluoromethylphenyl)indenyl)titanium dichloride
1,2-cyclohexanediylbis(2-isobutylindenyl)titanium dichloride
1,2-cyclohexanediylbis(2-isobutyl-4,5-benzindenyl)titanium dichloride
1,2-cyclohexanediylbis(2-isobutyl-4-phenylindenyl)titanium dichloride
1,2-cyclohexanediylbis(2-isobutyl-4-(4'-methylphenyl)indenyl)titanium dichloride
1,2-cyclohexanediylbis(2-isobutyl-4-(4'-ethylphenyl)indenyl)titanium dichloride
1,2-cyclohexanediylbis(2-isobutyl-4-(4'-propylphenyl)indenyl)titanium dichloride
1,2-cyclohexanediylbis(2-isobutyl-4-(4'-isopropylphenyl)indenyl)titanium dichloride
1,2-cyclohexanediylbis(2-isobutyl-4-(4'-tert-butylphenyl)indenyl)titanium dichloride
1,2-cyclohexanediylbis(2-isobutyl-4-(4'-methoxyphenyl)indenyl)titanium dichloride
1,2-cyclohexanediylbis(2-isobutyl-4-(1'-naphthyl)indenyl)titanium dichloride
1,2-cyclohexanediylbis(2-isobutyl-4-(9'-anthracenyl)indenyl)titanium dichloride
1,2-cyclohexanediylbis(2-isobutyl-4-(3',5'-di-tert-butylphenyl)indenyl)titanium dichloride
1,2-cyclohexanediylbis(2-isobutyl-4-(4'-trifluoromethylphenyl)indenyl)titanium dichloride
1,2-cyclohexanediylbis(2-butylindenyl)titanium dichloride
1,2-cyclohexanediylbis(2-butyl-4,5-benzindenyl)titanium dichloride
1,2-cyclohexanediylbis(2-butyl-4-phenylindenyl)titanium dichloride
1,2-cyclohexanediylbis(2-butyl-4-(4'-methylphenyl)indenyl)titanium dichloride
1,2-cyclohexanediylbis(2-butyl-4-(4'-ethylphenyl)indenyl)titanium dichloride
1,2-cyclohexanediylbis(2-butyl-4-(4'-propylphenyl)indenyl)titanium dichloride
1,2-cyclohexanediylbis(2-butyl-4-(4'-isopropylphenyl)indenyl)titanium dichloride
1,2-cyclohexanediylbis(2-butyl-4-(4'-tert-butylphenyl)indenyl)titanium dichloride
1,2-cyclohexanediylbis(2-butyl-4-(4'-methoxyphenyl)indenyl)titanium dichloride
1,2-cyclohexanediylbis(2-butyl-4-(1'-naphthyl)indenyl)titanium dichloride
1,2-cyclohexanediylbis(2-butyl-4-(9'-anthracenyl)indenyl)titanium dichloride
1,2-cyclohexanediylbis(2-butyl-4-(3',5'-di-tert-butylphenyl)indenyl)titanium dichloride
1,2-cyclohexanediylbis(2-butyl-4-(4'-trifluoromethylphenyl)indenyl)titanium dichloride
1,2-cyclohexanediylbis(2-tert-butylindenyl)titanium dichloride
1,2-cyclohexanediylbis(2-tert-butyl-4,5-benzindenyl)titanium dichloride
1,2-cyclohexanediylbis(2-tert-butyl-4-phenylindenyl)titanium dichloride
1,2-cyclohexanediylbis(2-tert-butyl-4-(4'-methylphenyl)indenyl)titanium dichloride
1,2-cyclohexanediylbis(2-tert-butyl-4-(4'-ethylphenyl)indenyl)titanium dichloride
1,2-cyclohexanediylbis(2-tert-butyl-4-(4'-propylphenyl)indenyl)titanium dichloride
1,2-cyclohexanediylbis(2-tert-butyl-4-(4'-isopropylphenyl)indenyl)titanium dichloride
1,2-cyclohexanediylbis(2-tert-butyl-4-(4'-tert-butylphenyl)indenyl)titanium dichloride
1,2-cyclohexanediylbis(2-tert-butyl-4-(4'-methoxyphenyl)indenyl)titanium dichloride
1,2-cyclohexanediylbis(2-tert-butyl-4-(1'-naphthyl)indenyl)titanium dichloride
1,2-cyclohexanediylbis(2-tert-butyl-4-(9'-anthracenyl)indenyl)titanium dichloride
1,2-cyclohexanediylbis(2-tert-butyl-4-(3',5'-di-tert-butylphenyl)indenyl)titanium dichloride
1,2-cyclohexanediylbis(2-tert-butyl-4-(4'-trifluoromethylphenyl)indenyl)titanium dichloride
1,2-cyclohexanediylbis(2-cyclopentylindenyl)titanium dichloride
1,2-cyclohexanediylbis(2-cyclopentyl-4,5-benzindenyl)titanium dichloride
1,2-cyclohexanediylbis(2-cyclopentyl-4-phenylindenyl)titanium dichloride
1,2-cyclohexanediylbis(2-cyclopentyl-4-(4'-methylphenyl)indenyl)titanium dichloride
1,2-cyclohexanediylbis(2-cyclopentyl-4-(4'-ethylphenyl)indenyl)titanium dichloride
1,2-cyclohexanediylbis(2-cyclopentyl-4-(4'-propylphenyl)indenyl)titanium dichloride 1,2-cyclohexanediylbis(2-cyclopentyl-4-(4'-isopropylphenyl)indenyl)titanium dichloride
1,2-cyclohexanediylbis(2-cyclopentyl-4-(4'-tert-butylphenyl)indenyl)titanium dichloride
1,2-cyclohexanediylbis(2-cyclopentyl-4-(4'-methoxyphenyl)indenyl)titanium dichloride
1,2-cyclohexanediylbis(2-cyclopentyl-4-(1'-naphthyl)indenyl)titanium dichloride
1,2-cyclohexanediylbis(2-cyclopentyl-4-(9'-anthracenyl)indenyl)titanium dichloride
1,2-cyclohexanediylbis(2-cyclopentyl-4-(3',5'-di-tert-butylphenyl)indenyl)titanium dichloride
1,2-cyclohexanediylbis(2-cyclopentyl-4-(4'-trifluoromethylphenyl)indenyl)titanium dichloride
1,2-cyclohexanediylbis(2-cyclohexylindenyl)titanium dichloride
1,2-cyclohexanediylbis(2-cyclohexyl-4,5-benzindenyl)titanium dichloride
1,2-cyclohexanediylbis(2-cyclohexyl-4-phenylindenyl)titanium dichloride
1,2-cyclohexanediylbis(2-cyclohexyl-4-(4'-methylphenyl)indenyl)titanium dichloride
1,2-cyclohexanediylbis(2-cyclohexyl-4-(4'-ethylphenyl)indenyl)titanium dichloride
1,2-cyclohexanediylbis(2-cyclohexyl-4-(4'-propylphenyl)indenyl)titanium dichloride
1,2-cyclohexanediylbis(2-cyclohexyl-4-(4'-isopropylphenyl)indenyl)titanium dichloride
1,2-cyclohexanediylbis(2-cyclohexyl-4-(4'-tert-butylphenyl)indenyl)titanium dichloride
1,2-cyclohexanediylbis(2-cyclohexyl-4-(4'-methoxyphenyl)indenyl)titanium dichloride
1,2-cyclohexanediylbis(2-cyclohexyl-4-(1'-naphthyl)indenyl)titanium dichloride
1,2-cyclohexanediylbis(2-cyclohexyl-4-(9'-anthracenyl)indenyl)titanium dichloride
1,2-cyclohexanediylbis(2-cyclohexyl-4-(3',5'-di-tert-butylphenyl)indenyl)titanium dichloride
1,2-cyclohexanediylbis(2-cyclohexyl-4-(4'-trifluoromethylphenyl)indenyl)titanium dichloride
1,2-cyclohexanediylbis(2-methylindenyl)hafnium dichloride
1,2-cyclohexanediylbis(2-methyl-4,5-benzindenyl)hafnium dichloride
1,2-cyclohexanediylbis(2-methyl-4-phenylindenyl)hafnium dichloride
1,2-cyclohexanediylbis(2-methyl-4-(4'-methylphenyl)indenyl)hafnium dichloride
1,2-cyclohexanediylbis(2-methyl-4-(4'-ethylphenyl)indenyl)hafnium dichloride
1,2-cyclohexanediylbis(2-methyl-4-(4'-propylphenyl)indenyl)hafnium dichloride
1,2-cyclohexanediylbis(2-methyl-4-(4'-isopropylphenyl)indenyl)hafnium dichloride
1,2-cyclohexanediylbis(2-methyl-4-(4'-tert-butylphenyl)indenyl)hafnium dichloride
1,2-cyclohexanediylbis(2-methyl-4-(4'-methoxyphenyl)indenyl)hafnium dichloride
1,2-cyclohexanediylbis(2-methyl-4-(1'-naphthyl)indenyl)hafnium dichloride
1,2-cyclohexanediylbis(2-methyl-4-(9'-anthracenyl)indenyl)hafnium dichloride
1,2-cyclohexanediylbis(2-methyl-4-(3',5'-di-tert-butylphenyl)indenyl)hafnium dichloride
1,2-cyclohexanediylbis(2-methyl-4-(4'-trifluoromethylphenyl)indenyl)hafnium dichloride
1,2-cyclohexanediylbis(2-ethylindenyl)hafnium dichloride
1,2-cyclohexanediylbis(2-ethyl-4,5-benzindenyl)hafnium dichloride
1,2-cyclohexanediylbis(2-ethyl-4-phenylindenyl)hafnium dichloride
1,2-cyclohexanediylbis(2-ethyl-4-(4'-methylphenyl)indenyl)hafnium dichloride
1,2-cyclohexanediylbis(2-ethyl-4-(4'-ethylphenyl)indenyl)hafnium dichloride
1,2-cyclohexanediylbis(2-ethyl-4-(4'-propylphenyl)indenyl)hafnium dichloride
1,2-cyclohexanediylbis(2-ethyl-4-(4'-isopropylphenyl)indenyl)hafnium dichloride
1,2-cyclohexanediylbis(2-ethyl-4-(4'-tert-butylphenyl)indenyl)hafnium dichloride
1,2-cyclohexanediylbis(2-ethyl-4-(4'-methoxyphenyl)indenyl)hafnium dichloride
1,2-cyclohexanediylbis(2-ethyl-4-(1'-naphthyl)indenyl)hafnium dichloride
1,2-cyclohexanediylbis(2-ethyl-4-(9'-anthracenyl)indenyl)hafnium dichloride
1,2-cyclohexanediylbis(2-ethyl-4-(3',5'-di-tert-butylphenyl)indenyl)hafnium dichloride
1,2-cyclohexanediylbis(2-ethyl-4-(4'-trifluoromethylphenyl)indenyl)hafnium dichloride
1,2-cyclohexanediylbis(2-propylindenyl)hafnium dichloride
1,2-cyclohexanediylbis(2-propyl-4,5-benzindenyl)hafnium dichloride
1,2-cyclohexanediylbis(2-propyl-4-phenylindenyl)hafnium dichloride
1,2-cyclohexanediylbis(2-propyl-4-(4'-methylphenyl)indenyl)hafnium dichloride
1,2-cyclohexanediylbis(2-propyl-4-(4'-ethylphenyl)indenyl)hafnium dichloride
1,2-cyclohexanediylbis(2-propyl-4-(4'-propylphenyl)indenyl)hafnium dichloride
1,2-cyclohexanediylbis(2-propyl-4-(4'-isopropylphenyl)indenyl)hafnium dichloride
1,2-cyclohexanediylbis(2-propyl-4-(4'-tert-butylphenyl)indenyl)hafnium dichloride
1,2-cyclohexanediylbis(2-propyl-4-(4'-methoxyphenyl)indenyl)hafnium dichloride
1,2-cyclohexanediylbis(2-propyl-4-(1'-naphthyl)indenyl)hafnium dichloride
1,2-cyclohexanediylbis(2-propyl-4-(9'-anthracenyl)indenyl)hafnium dichloride
1,2-cyclohexanediylbis(2-propyl-4-(3',5'-di-tert-butylphenyl)indenyl)hafnium dichloride
1,2-cyclohexanediylbis(2-propyl-4-(4'-trifluoromethylphenyl)indenyl)hafnium dichloride
1,2-cyclohexanediylbis(2-isopropylindenyl)hafnium dichloride
1,2-cyclohexanediylbis(2-isopropyl-4,5-benzindenyl)hafnium dichloride
1,2-cyclohexanediylbis(2-isopropyl-4-phenylindenyl)hafnium dichloride
1,2-cyclohexanediylbis(2-isopropyl-4-(4'-methylphenyl)indenyl)hafnium dichloride
1,2-cyclohexanediylbis(2-isopropyl-4-(4'-ethylphenyl)indenyl)hafnium dichloride
1,2-cyclohexanediylbis(2-isopropyl-4-(4'-propylphenyl)indenyl)hafnium dichloride
1,2-cyclohexanediylbis(2-isopropyl-4-(4'-isopropylphenyl)indenyl)hafnium dichloride
1,2-cyclohexanediylbis(2-isopropyl-4-(4'-tert-butylphenyl)indenyl)hafnium dichloride
1,2-cyclohexanediylbis(2-isopropyl-4-(4'-methoxyphenyl)indenyl)hafnium dichloride 1,2-cyclohexanediylbis(2-isopropyl-4-(1'-naphthyl)indenyl)hafnium dichloride
1,2-cyclohexanediylbis(2-isopropyl-4-(9'-anthracenyl)indenyl)hafnium dichloride
1,2-cyclohexanediylbis(2-isopropyl-4-(3',5'-di-tert-butylphenyl)indenyl)hafnium dichloride
1,2-cyclohexanediylbis(2-isopropyl-4-(4'-trifluoromethylphenyl)indenyl)hafnium dichloride
1,2-cyclohexanediylbis(2-isobutylindenyl)hafnium dichloride
1,2-cyclohexanediylbis(2-isobutyl-4,5-benzindenyl)hafnium dichloride
1,2-cyclohexanediylbis(2-isobutyl-4-phenylindenyl)hafnium dichloride
1,2-cyclohexanediylbis(2-isobutyl-4-(4'-methylphenyl)indenyl)hafnium dichloride
1,2-cyclohexanediylbis(2-isobutyl-4-(4'-ethylphenyl)indenyl)hafnium dichloride
1,2-cyclohexanediylbis(2-isobutyl-4-(4'-propylphenyl)indenyl)hafnium dichloride
1,2-cyclohexanediylbis(2-isobutyl-4-(4'-isopropylphenyl)indenyl)hafnium dichloride
1,2-cyclohexanediylbis(2-isobutyl-4-(4'-tert-butylphenyl)indenyl)hafnium dichloride
1,2-cyclohexanediylbis(2-isobutyl-4-(4'-methoxyphenyl)indenyl)hafnium dichloride
1,2-cyclohexanediylbis(2-isobutyl-4-(1'-naphthyl)indenyl)hafnium dichloride
1,2-cyclohexanediylbis(2-isobutyl-4-(9'-anthracenyl)indenyl)hafnium dichloride
1,2-cyclohexanediylbis(2-isobutyl-4-(3',5'-di-tert-butylphenyl)indenyl)hafnium dichloride
1,2-cyclohexanediylbis(2-isobutyl-4-(4'-trifluoromethylphenyl)indenyl)hafnium dichloride
1,2-cyclohexanediylbis(2-butylindenyl)hafnium dichloride
1,2-cyclohexanediylbis(2-butyl-4,5-benzindenyl)hafnium dichloride
1,2-cyclohexanediylbis(2-butyl-4-phenylindenyl)hafnium dichloride
1,2-cyclohexanediylbis(2-butyl-4-(4'-methylphenyl)indenyl)hafnium dichloride
1,2-cyclohexanediylbis(2-butyl-4-(4'-ethylphenyl)indenyl)hafnium dichloride
1,2-cyclohexanediylbis(2-butyl-4-(4'-propylphenyl)indenyl)hafnium dichloride
1,2-cyclohexanediylbis(2-butyl-4-(4'-isopropylphenyl)indenyl)hafnium dichloride
1,2-cyclohexanediylbis(2-butyl-4-(4'-tert-butylphenyl)indenyl)hafnium dichloride
1,2-cyclohexanediylbis(2-butyl-4-(4'-methoxyphenyl)indenyl)hafnium dichloride
1,2-cyclohexanediylbis(2-butyl-4-(1'-naphthyl)indenyl)hafnium dichloride
1,2-cyclohexanediylbis(2-butyl-4-(9'-anthracenyl)indenyl)hafnium dichloride
1,2-cyclohexanediylbis(2-butyl-4-(3',5'-di-tert-butylphenyl)indenyl)hafnium dichloride
1,2-cyclohexanediylbis(2-butyl-4-(4'-trifluoromethylphenyl)indenyl)hafnium dichloride
1,2-cyclohexanediylbis(2-tert-butylindenyl)hafnium dichloride
1,2-cyclohexanediylbis(2-tert-butyl-4,5-benzindenyl)hafnium dichloride
1,2-cyclohexanediylbis(2-tert-butyl-4-phenylindenyl)hafnium dichloride
1,2-cyclohexanediylbis(2-tert-butyl-4-(4'-methylphenyl)indenyl)hafnium dichloride
1,2-cyclohexanediylbis(2-tert-butyl-4-(4'-ethylphenyl)indenyl)hafnium dichloride
1,2-cyclohexanediylbis(2-tert-butyl-4-(4'-propylphenyl)indenyl)hafnium dichloride
1,2-cyclohexanediylbis(2-tert-butyl-4-(4'-isopropylphenyl)indenyl)hafnium dichloride
1,2-cyclohexanediylbis(2-tert-butyl-4-(4'-tert-butylphenyl)indenyl)hafnium dichloride
1,2-cyclohexanediylbis(2-tert-butyl-4-(4'-methoxyphenyl)indenyl)hafnium dichloride
1,2-cyclohexanediylbis(2-tert-butyl-4-(1'-naphthyl)indenyl)hafnium dichloride
1,2-cyclohexanediylbis(2-tert-butyl-4-(9'-anthracenyl)indenyl)hafnium dichloride
1,2-cyclohexanediylbis(2-tert-butyl-4-(3',5'-di-tert-butylphenyl)indenyl)hafnium dichloride
1,2-cyclohexanediylbis(2-tert-butyl-4-(4'-trifluoromethylphenyl)indenyl)hafnium dichloride
1,2-cyclohexanediylbis(2-cyclopentylindenyl)hafnium dichloride
1,2-cyclohexanediylbis(2-cyclopentyl-4,5-benzindenyl)hafnium dichloride
1,2-cyclohexanediylbis(2-cyclopentyl-4-phenylindenyl)hafnium dichloride
1,2-cyclohexanediylbis(2-cyclopentyl-4-(4'-methylphenyl)indenyl)hafnium dichloride
1,2-cyclohexanediylbis(2-cyclopentyl-4-(4'-ethylphenyl)indenyl)hafnium dichloride
1,2-cyclohexanediylbis(2-cyclopentyl-4-(4'-propylphenyl)indenyl)hafnium dichloride
1,2-cyclohexanediylbis(2-cyclopentyl-4-(4'-isopropylphenyl)indenyl)hafnium dichloride
1,2-cyclohexanediylbis(2-cyclopentyl-4-(4'-tert-butylphenyl)indenyl)hafnium dichloride
1,2-cyclohexanediylbis(2-cyclopentyl-4-(4'-methoxyphenyl)indenyl)hafnium dichloride
1,2-cyclohexanediylbis(2-cyclopentyl-4-(1'-naphthyl)indenyl)hafnium dichloride
1,2-cyclohexanediylbis(2-cyclopentyl-4-(9'-anthracenyl)indenyl)hafnium dichloride
1,2-cyclohexanediylbis(2-cyclopentyl-4-(3',5'-di-tert-butylphenyl)indenyl)hafnium dichloride
1,2-cyclohexanediylbis(2-cyclopentyl-4-(4'-trifluoromethylphenyl)indenyl)hafnium dichloride
1,2-cyclohexanediylbis(2-cyclohexylindenyl)hafnium dichloride
1,2-cyclohexanediylbis(2-cyclohexyl-4,5-benzindenyl)hafnium dichloride
1,2-cyclohexanediylbis(2-cyclohexyl-4-phenylindenyl)hafnium dichloride
1,2-cyclohexanediylbis(2-cyclohexyl-4-(4'-methylphenyl)indenyl)hafnium dichloride
1,2-cyclohexanediylbis(2-cyclohexyl-4-(4'-ethylphenyl)indenyl)hafnium dichloride
1,2-cyclohexanediylbis(2-cyclohexyl-4-(4'-propylphenyl)indenyl)hafnium dichloride
1,2-cyclohexanediylbis(2-cyclohexyl-4-(4'-isopropylphenyl)indenyl)hafnium dichloride
1,2-cyclohexanediylbis(2-cyclohexyl-4-(4'-tert-butylphenyl)indenyl)hafnium dichloride
1,2-cyclohexanediylbis(2-cyclohexyl-4-(4'-methoxyphenyl)indenyl)hafnium dichloride
1,2-cyclohexanediylbis(2-cyclohexyl-4-(1'-naphthyl)indenyl)hafnium dichloride
1,2-cyclohexanediylbis(2-cyclohexyl-4-(9'-anthracenyl)indenyl)hafnium dichloride
1,2-cyclohexanediylbis(2-cyclohexyl-4-(3',5'-di-tert-butylphenyl)indenyl)hafnium dichloride 1,2-cyclohexanediylbis(2-cyclohexyl-4-(4'-trifluoromethylphenyl)indenyl)hafnium dichloride
1,3-propanediylbis(2-methylindenyl)zirconium dichloride
1,3-propanediylbis(2-methyl-4,5-benzindenyl)zirconium dichloride
1,3-propanediylbis(2-methyl-4-phenylindenyl)zirconium dichloride
1,3-propanediylbis(2-methyl-4-(4'-methylphenyl)indenyl)zirconium dichloride
1,3-propanediylbis(2-methyl-4-(4'-ethylphenyl)indenyl)zirconium dichloride
1,3-propanediylbis(2-methyl-4-(4'-propylphenyl)indenyl)zirconium dichloride
1,3-propanediylbis(2-methyl-4-(4'-isopropylphenyl)indenyl)zirconium dichloride
1,3-propanediylbis(2-methyl-4-(4'-tert-butylphenyl)indenyl)zirconium dichloride
1,3-propanediylbis(2-methyl-4-(4'-methoxyphenyl)indenyl)zirconium dichloride
1,3-propanediylbis(2-methyl-4-(1'-naphthyl)indenyl)zirconium dichloride
1,3-propanediylbis(2-methyl-4-(9'-anthracenyl)indenyl)zirconium dichloride
1,3-propanediylbis(2-methyl-4-(3',5'-di-tert-butylphenyl)indenyl)zirconium dichloride
1,3-propanediylbis(2-methyl-4-(4'-trifluoromethylphenyl)indenyl)zirconium dichloride
1,3-propanediylbis(2-ethylindenyl)zirconium dichloride
1,3-propanediylbis(2-ethyl-4,5-benzindenyl)zirconium dichloride
1,3-propanediylbis(2-ethyl-4-phenylindenyl)zirconium dichloride
1,3-propanediylbis(2-ethyl-4-(4'-methylphenyl)indenyl)zirconium dichloride
1,3-propanediylbis(2-ethyl-4-(4'-ethylphenyl)indenyl)zirconium dichloride
1,3-propanediylbis(2-ethyl-4-(4'-propylphenyl)indenyl)zirconium dichloride
1,3-propanediylbis(2-ethyl-4-(4'-isopropylphenyl)indenyl)zirconium dichloride
1,3-propanediylbis(2-ethyl-4-(4'-tert-butylphenyl)indenyl)zirconium dichloride
1,3-propanediylbis(2-ethyl-4-(4'-methoxyphenyl)indenyl)zirconium dichloride
1,3-propanediylbis(2-ethyl-4-(1'-naphthyl)indenyl)zirconium dichloride
1,3-propanediylbis(2-ethyl-4-(9'-anthracenyl)indenyl)zirconium dichloride
1,3-propanediylbis(2-ethyl-4-(3',5'-di-tert-butylphenyl)indenyl)zirconium dichloride
1,3-propanediylbis(2-ethyl-4-(4'-trifluoromethylphenyl)indenyl)zirconium dichloride
1,3-propanediylbis(2-propylindenyl)zirconium dichloride
1,3-propanediylbis(2-propyl-4,5-benzindenyl)zirconium dichloride
1,3-propanediylbis(2-propyl-4-phenylindenyl)zirconium dichloride
1,3-propanediylbis(2-propyl-4-(4'-methylphenyl)indenyl)zirconium dichloride
1,3-propanediylbis(2-propyl-4-(4'-ethylphenyl)indenyl)zirconium dichloride
1,3-propanediylbis(2-propyl-4-(4'-propylphenyl)indenyl)zirconium dichloride
1,3-propanediylbis(2-propyl-4-(4'-isopropylphenyl)indenyl)zirconium dichloride
1,3-propanediylbis(2-propyl-4-(4'-tert-butylphenyl)indenyl)zirconium dichloride
1,3-propanediylbis(2-propyl-4-(4'-methoxyphenyl)indenyl)zirconium dichloride
1,3-propanediylbis(2-propyl-4-(1'-naphthyl)indenyl)zirconium dichloride
1,3-propanediylbis(2-propyl-4-(9'-anthracenyl)indenyl)zirconium dichloride
1,3-propanediylbis(2-propyl-4-(3',5'-di-tert-butylphenyl)indenyl)zirconium dichloride
1,3-propanediylbis(2-propyl-4-(4'-trifluoromethylphenyl)indenyl)zirconium dichloride
1,3-propanediylbis(2-isopropylindenyl)zirconium dichloride
1,3-propanediylbis(2-isopropyl-4,5-benzindenyl)zirconium dichloride
1,3-propanediylbis(2-isopropyl-4-phenylindenyl)zirconium dichloride
1,3-propanediylbis(2-isopropyl-4-(4'-methylphenyl)indenyl)zirconium dichloride
1,3-propanediylbis(2-isopropyl-4-(4'-ethylphenyl)indenyl)zirconium dichloride
1,3-propanediylbis(2-isopropyl-4-(4'-propylphenyl)indenyl)zirconium dichloride
1,3-propanediylbis(2-isopropyl-4-(4'-isopropylphenyl)indenyl)zirconium dichloride
1,3-propanediylbis(2-isopropyl-4-(4'-tert-butylphenyl)indenyl)zirconium dichloride
1,3-propanediylbis(2-isopropyl-4-(4'-methoxyphenyl)indenyl)zirconium dichloride
1,3-propanediylbis(2-isopropyl-4-(1'-naphthyl)indenyl)zirconium dichloride
1,3-propanediylbis(2-isopropyl-4-(9'-anthracenyl)indenyl)zirconium dichloride
1,3-propanediylbis(2-isopropyl-4-(3',5'-di-tert-butylphenyl)indenyl)zirconium dichloride
1,3-propanediylbis(2-isopropyl-4-(4'-trifluoromethylphenyl)indenyl)zirconium dichloride
1,3-propanediylbis(2-isobutylindenyl)zirconium dichloride
1,3-propanediylbis(2-isobutyl-4,5-benzindenyl)zirconium dichloride
1,3-propanediylbis(2-isobutyl-4-phenylindenyl)zirconium dichloride
1,3-propanediylbis(2-isobutyl-4-(4'-methylphenyl)indenyl)zirconium dichloride
1,3-propanediylbis(2-isobutyl-4-(4'-ethylphenyl)indenyl)zirconium dichloride
1,3-propanediylbis(2-isobutyl-4-(4'-propylphenyl)indenyl)zirconium dichloride
1,3-propanediylbis(2-isobutyl-4-(4'-isopropylphenyl)indenyl)zirconium dichloride
1,3-propanediylbis(2-isobutyl-4-(4'-tert-butylphenyl)indenyl)zirconium dichloride
1,3-propanediylbis(2-isobutyl-4-(4'-methoxyphenyl)indenyl)zirconium dichloride
1,3-propanediylbis(2-isobutyl-4-(1'-naphthyl)indenyl)zirconium dichloride
1,3-propanediylbis(2-isobutyl-4-(9'-anthracenyl)indenyl)zirconium dichloride
1,3-propanediylbis(2-isobutyl-4-(3',5'-di-tert-butylphenyl)indenyl)zirconium dichloride
1,3-propanediylbis(2-isobutyl-4-(4'-trifluoromethylphenyl)indenyl)zirconium dichloride
1,3-propanediylbis(2-butylindenyl)zirconium dichloride
1,3-propanediylbis(2-butyl-4,5-benzindenyl)zirconium dichloride
1,3-propanediylbis(2-butyl-4-phenylindenyl)zirconium dichloride
1,3-propanediylbis(2-butyl-4-(4'-methylphenyl)indenyl)zirconium dichloride 1,3-propanediylbis(2-butyl-4-(4'-ethylphenyl)indenyl)zirconium dichloride
1,3-propanediylbis(2-butyl-4-(4'-propylphenyl)indenyl)zirconium dichloride
1,3-propanediylbis(2-butyl-4-(4'-isopropylphenyl)indenyl)zirconium dichloride
1,3-propanediylbis(2-butyl-4-(4'-tert-butylphenyl)indenyl)zirconium dichloride
1,3-propanediylbis(2-butyl-4-(4'-methoxyphenyl)indenyl)zirconium dichloride
1,3-propanediylbis(2-butyl-4-(1'-naphthyl)indenyl)zirconium dichloride
1,3-propanediylbis(2-butyl-4-(9'-anthracenyl)indenyl)zirconium dichloride
1,3-propanediylbis(2-butyl-4-(3',5'-di-tert-butylphenyl)indenyl)zirconium dichloride
1,3-propanediylbis(2-butyl-4-(4'-trifluoromethylphenyl)indenyl)zirconium dichloride
1,3-propanediylbis(2-tert-butylindenyl)zirconium dichloride
1,3-propanediylbis(2-tert-butyl-4,5-benzindenyl)zirconium dichloride
1,3-propanediylbis(2-tert-butyl-4-phenylindenyl)zirconium dichloride
1,3-propanediylbis(2-tert-butyl-4-(4'-methylphenyl)indenyl)zirconium dichloride
1,3-propanediylbis(2-tert-butyl-4-(4'-ethylphenyl)indenyl)zirconium dichloride
1,3-propanediylbis(2-tert-butyl-4-(4'-propylphenyl)indenyl)zirconium dichloride
1,3-propanediylbis(2-tert-butyl-4-(4'-isopropylphenyl)indenyl)zirconium dichloride
1,3-propanediylbis(2-tert-butyl-4-(4'-tert-butylphenyl)indenyl)zirconium dichloride
1,3-propanediylbis(2-tert-butyl-4-(4'-methoxyphenyl)indenyl)zirconium dichloride
1,3-propanediylbis(2-tert-butyl-4-(1'-naphthyl)indenyl)zirconium dichloride
1,3-propanediylbis(2-tert-butyl-4-(9'-anthracenyl)indenyl)zirconium dichloride
1,3-propanediylbis(2-tert-butyl-4-(3',5'-di-tert-butylphenyl)indenyl)zirconium dichloride
1,3-propanediylbis(2-tert-butyl-4-(4'-trifluoromethylphenyl)indenyl)zirconium dichloride
1,3-propanediylbis(2-cyclopentylindenyl)zirconium dichloride
1,3-propanediylbis(2-cyclopentyl-4,5-benzindenyl)zirconium dichloride
1,3-propanediylbis(2-cyclopentyl-4-phenylindenyl)zirconium dichloride
1,3-propanediylbis(2-cyclopentyl-4-(4'-methylphenyl)indenyl)zirconium dichloride
1,3-propanediylbis(2-cyclopentyl-4-(4'-ethylphenyl)indenyl)zirconium dichloride
1,3-propanediylbis(2-cyclopentyl-4-(4'-propylphenyl)indenyl)zirconium dichloride
1,3-propanediylbis(2-cyclopentyl-4-(4'-isopropylphenyl)indenyl)zirconium dichloride
1,3-propanediylbis(2-cyclopentyl-4-(4'-tert-butylphenyl)indenyl)zirconium dichloride
1,3-propanediylbis(2-cyclopentyl-4-(4'-methoxyphenyl)indenyl)zirconium dichloride
1,3-propanediylbis(2-cyclopentyl-4-(1'-naphthyl)indenyl)zirconium dichloride
1,3-propanediylbis(2-cyclopentyl-4-(9'-anthracenyl)indenyl)zirconium dichloride
1,3-propanediylbis(2-cyclopentyl-4-(3',5'-di-tert-butylphenyl)indenyl)zirconium dichloride
1,3-propanediylbis(2-cyclopentyl-4-(4'-trifluoromethylphenyl)indenyl)zirconium dichloride
1,3-propanediylbis(2-cyclohexylindenyl)zirconium dichloride
1,3-propanediylbis(2-cyclohexyl-4,5-benzindenyl)zirconium dichloride
1,3-propanediylbis(2-cyclohexyl-4-phenylindenyl)zirconium dichloride
1,3-propanediylbis(2-cyclohexyl-4-(4'-methylphenyl)indenyl)zirconium dichloride
1,3-propanediylbis(2-cyclohexyl-4-(4'-ethylphenyl)indenyl)zirconium dichloride
1,3-propanediylbis(2-cyclohexyl-4-(4'-propylphenyl)indenyl)zirconium dichloride
1,3-propanediylbis(2-cyclohexyl-4-(4'-isopropylphenyl)indenyl)zirconium dichloride
1,3-propanediylbis(2-cyclohexyl-4-(4'-tert-butylphenyl)indenyl)zirconium dichloride
1,3-propanediylbis(2-cyclohexyl-4-(4'-methoxyphenyl)indenyl)zirconium dichloride
1,3-propanediylbis(2-cyclohexyl-4-(1'-naphthyl)indenyl)zirconium dichloride
1,3-propanediylbis(2-cyclohexyl-4-(9'-anthracenyl)indenyl)zirconium dichloride
1,3-propanediylbis(2-cyclohexyl-4-(3',5'-di-tert-butylphenyl)indenyl)zirconium dichloride
1,3-propanediylbis(2-cyclohexyl-4-(4'-trifluoromethylphenyl)indenyl)zirconium dichloride
1,3-propanediylbis(2-methylindenyl)titanium dichloride
1,3-propanediylbis(2-methyl-4,5-benzindenyl)titanium dichloride
1,3-propanediylbis(2-methyl-4-phenylindenyl)titanium dichloride
1,3-propanediylbis(2-methyl-4-(4'-methylphenyl)indenyl)titanium dichloride
1,3-propanediylbis(2-methyl-4-(4'-ethylphenyl)indenyl)titanium dichloride
1,3-propanediylbis(2-methyl-4-(4'-propylphenyl)indenyl)titanium dichloride
1,3-propanediylbis(2-methyl-4-(4'-isopropylphenyl)indenyl)titanium dichloride
1,3-propanediylbis(2-methyl-4-(4'-tert-butylphenyl)indenyl)titanium dichloride
1,3-propanediylbis(2-methyl-4-(4'-methoxyphenyl)indenyl)titanium dichloride
1,3-propanediylbis(2-methyl-4-(1'-naphthyl)indenyl)titanium dichloride
1,3-propanediylbis(2-methyl-4-(9'-anthracenyl)indenyl)titanium dichloride
1,3-propanediylbis(2-methyl-4-(3',5'-di-tert-butylphenyl)indenyl)titanium dichloride
1,3-propanediylbis(2-methyl-4-(4'-trifluoromethylphenyl)indenyl)titanium dichloride
1,3-propanediylbis(2-ethylindenyl)titanium dichloride
1,3-propanediylbis(2-ethyl-4,5-benzindenyl)titanium dichloride
1,3-propanediylbis(2-ethyl-4-phenylindenyl)titanium dichloride
1,3-propanediylbis(2-ethyl-4-(4'-methylphenyl)indenyl)titanium dichloride
1,3-propanediylbis(2-ethyl-4-(4'-ethylphenyl)indenyl)titanium dichloride
1,3-propanediylbis(2-ethyl-4-(4'-propylphenyl)indenyl)titanium dichloride
1,3-propanediylbis(2-ethyl-4-(4'-isopropylphenyl)indenyl)titanium dichloride
1,3-propanediylbis(2-ethyl-4-(4'-tert-butylphenyl)indenyl)titanium dichloride 1,3-propanediylbis(2-ethyl-4-(4'-methoxyphenyl)indenyl)titanium dichloride
1,3-propanediylbis(2-ethyl-4-(1'-naphthyl)indenyl)titanium dichloride
1,3-propanediylbis(2-ethyl-4-(9'-anthracenyl)indenyl)titanium dichloride
1,3-propanediylbis(2-ethyl-4-(3',5'-di-tert-butylphenyl)indenyl)titanium dichloride
1,3-propanediylbis(2-ethyl-4-(4'-trifluoromethylphenyl)indenyl)titanium dichloride
1,3-propanediylbis(2-propylindenyl)titanium dichloride
1,3-propanediylbis(2-propyl-4,5-benzindenyl)titanium dichloride
1,3-propanediylbis(2-propyl-4-phenylindenyl)titanium dichloride
1,3-propanediylbis(2-propyl-4-(4'-methylphenyl)indenyl)titanium dichloride
1,3-propanediylbis(2-propyl-4-(4'-ethylphenyl)indenyl)titanium dichloride
1,3-propanediylbis(2-propyl-4-(4'-propylphenyl)indenyl)titanium dichloride
1,3-propanediylbis(2-propyl-4-(4'-isopropylphenyl)indenyl)titanium dichloride
1,3-propanediylbis(2-propyl-4-(4'-tert-butylphenyl)indenyl)titanium dichloride
1,3-propanediylbis(2-propyl-4-(4'-methoxyphenyl)indenyl)titanium dichloride
1,3-propanediylbis(2-propyl-4-(1'-naphthyl)indenyl)titanium dichloride
1,3-propanediylbis(2-propyl-4-(9'-anthracenyl)indenyl)titanium dichloride
1,3-propanediylbis(2-propyl-4-(3',5'-di-tert-butylphenyl)indenyl)titanium dichloride
1,3-propanediylbis(2-propyl-4-(4'-trifluoromethylphenyl)indenyl)titanium dichloride
1,3-propanediylbis(2-isopropylindenyl)titanium dichloride
1,3-propanediylbis(2-isopropyl-4,5-benzindenyl)titanium dichloride
1,3-propanediylbis(2-isopropyl-4-phenylindenyl)titanium dichloride
1,3-propanediylbis(2-isopropyl-4-(4'-methylphenyl)indenyl)titanium dichloride
1,3-propanediylbis(2-isopropyl-4-(4'-ethylphenyl)indenyl)titanium dichloride
1,3-propanediylbis(2-isopropyl-4-(4'-propylphenyl)indenyl)titanium dichloride
1,3-propanediylbis(2-isopropyl-4-(4'-isopropylphenyl)indenyl)titanium dichloride
1,3-propanediylbis(2-isopropyl-4-(4'-tert-butylphenyl)indenyl)titanium dichloride
1,3-propanediylbis(2-isopropyl-4-(4'-methoxyphenyl)indenyl)titanium dichloride
1,3-propanediylbis(2-isopropyl-4-(1'-naphthyl)indenyl)titanium dichloride
1,3-propanediylbis(2-isopropyl-4-(9'-anthracenyl)indenyl)titanium dichloride
1,3-propanediylbis(2-isopropyl-4-(3',5'-di-tert-butylphenyl)indenyl)titanium dichloride
1,3-propanediylbis(2-isopropyl-4-(4'-trifluoromethylphenyl)indenyl)titanium dichloride
1,3-propanediylbis(2-isobutylindenyl)titanium dichloride
1,3-propanediylbis(2-isobutyl-4,5-benzindenyl)titanium dichloride
1,3-propanediylbis(2-isobutyl-4-phenylindenyl)titanium dichloride
1,3-propanediylbis(2-isobutyl-4-(4'-methylphenyl)indenyl)titanium dichloride
1,3-propanediylbis(2-isobutyl-4-(4'-ethylphenyl)indenyl)titanium dichloride
1,3-propanediylbis(2-isobutyl-4-(4'-propylphenyl)indenyl)titanium dichloride
1,3-propanediylbis(2-isobutyl-4-(4'-isopropylphenyl)indenyl)titanium dichloride
1,3-propanediylbis(2-isobutyl-4-(4'-tert-butylphenyl)indenyl)titanium dichloride
1,3-propanediylbis(2-isobutyl-4-(4'-methoxyphenyl)indenyl)titanium dichloride
1,3-propanediylbis(2-isobutyl-4-(1'-naphthyl)indenyl)titanium dichloride
1,3-propanediylbis(2-isobutyl-4-(9'-anthracenyl)indenyl)titanium dichloride
1,3-propanediylbis(2-isobutyl-4-(3',5'-di-tert-butylphenyl)indenyl)titanium dichloride
1,3-propanediylbis(2-isobutyl-4-(4'-trifluoromethylphenyl)indenyl)titanium dichloride
1,3-propanediylbis(2-butylindenyl)titanium dichloride
1,3-propanediylbis(2-butyl-4,5-benzindenyl)titanium dichloride
1,3-propanediylbis(2-butyl-4-phenylindenyl)titanium dichloride
1,3-propanediylbis(2-butyl-4-(4'-methylphenyl)indenyl)titanium dichloride
1,3-propanediylbis(2-butyl-4-(4'-ethylphenyl)indenyl)titanium dichloride
1,3-propanediylbis(2-butyl-4-(4'-propylphenyl)indenyl)titanium dichloride
1,3-propanediylbis(2-butyl-4-(4'-isopropylphenyl)indenyl)titanium dichloride
1,3-propanediylbis(2-butyl-4-(4'-tert-butylphenyl)indenyl)titanium dichloride
1,3-propanediylbis(2-butyl-4-(4'-methoxyphenyl)indenyl)titanium dichloride
1,3-propanediylbis(2-butyl-4-(1'-naphthyl)indenyl)titanium dichloride
1,3-propanediylbis(2-butyl-4-(9'-anthracenyl)indenyl)titanium dichloride
1,3-propanediylbis(2-butyl-4-(3',5'-di-tert-butylphenyl)indenyl)titanium dichloride
1,3-propanediylbis(2-butyl-4-(4'-trifluoromethylphenyl)indenyl)titanium dichloride
1,3-propanediylbis(2-tert-butylindenyl)titanium dichloride
1,3-propanediylbis(2-tert-butyl-4,5-benzindenyl)titanium dichloride
1,3-propanediylbis(2-tert-butyl-4-phenylindenyl)titanium dichloride
1,3-propanediylbis(2-tert-butyl-4-(4'-methylphenyl)indenyl)titanium dichloride
1,3-propanediylbis(2-tert-butyl-4-(4'-ethylphenyl)indenyl)titanium dichloride
1,3-propanediylbis(2-tert-butyl-4-(4'-propylphenyl)indenyl)titanium dichloride
1,3-propanediylbis(2-tert-butyl-4-(4'-isopropylphenyl)indenyl)titanium dichloride
1,3-propanediylbis(2-tert-butyl-4-(4'-tert-butylphenyl)indenyl)titanium dichloride
1,3-propanediylbis(2-tert-butyl-4-(4'-methoxyphenyl)indenyl)titanium dichloride
1,3-propanediylbis(2-tert-butyl-4-(1'-naphthyl)indenyl)titanium dichloride
1,3-propanediylbis(2-tert-butyl-4-(9'-anthracenyl)indenyl)titanium dichloride
1,3-propanediylbis(2-tert-butyl-4-(3',5'-di-tert-butylphenyl)indenyl)titanium dichloride
1,3-propanediylbis(2-tert-butyl-4-(4'-trifluoromethylphenyl)indenyl)titanium dichloride 1,3-propanediylbis(2-cyclopentylindenyl)titanium dichloride
1,3-propanediylbis(2-cyclopentyl-4,5-benzindenyl)titanium dichloride
1,3-propanediylbis(2-cyclopentyl-4-phenylindenyl)titanium dichloride
1,3-propanediylbis(2-cyclopentyl-4-(4'-methylphenyl)indenyl)titanium dichloride
1,3-propanediylbis(2-cyclopentyl-4-(4'-ethylphenyl)indenyl)titanium dichloride
1,3-propanediylbis(2-cyclopentyl-4-(4'-propylphenyl)indenyl)titanium dichloride
1,3-propanediylbis(2-cyclopentyl-4-(4'-isopropylphenyl)indenyl)titanium dichloride
1,3-propanediylbis(2-cyclopentyl-4-(4'-tert-butylphenyl)indenyl)titanium dichloride
1,3-propanediylbis(2-cyclopentyl-4-(4'-methoxyphenyl)indenyl)titanium dichloride
1,3-propanediylbis(2-cyclopentyl-4-(1'-naphthyl)indenyl)titanium dichloride
1,3-propanediylbis(2-cyclopentyl-4-(9'-anthracenyl)indenyl)titanium dichloride
1,3-propanediylbis(2-cyclopentyl-4-(3',5'-di-tert-butylphenyl)indenyl)titanium dichloride
1,3-propanediylbis(2-cyclopentyl-4-(4'-trifluoromethylphenyl)indenyl)titanium dichloride
1,3-propanediylbis(2-cyclohexylindenyl)titanium dichloride
1,3-propanediylbis(2-cyclohexyl-4,5-benzindenyl)titanium dichloride
1,3-propanediylbis(2-cyclohexyl-4-phenylindenyl)titanium dichloride
1,3-propanediylbis(2-cyclohexyl-4-(4'-methylphenyl)indenyl)titanium dichloride
1,3-propanediylbis(2-cyclohexyl-4-(4'-ethylphenyl)indenyl)titanium dichloride
1,3-propanediylbis(2-cyclohexyl-4-(4'-propylphenyl)indenyl)titanium dichloride
1,3-propanediylbis(2-cyclohexyl-4-(4'-isopropylphenyl)indenyl)titanium dichloride
1,3-propanediylbis(2-cyclohexyl-4-(4'-tert-butylphenyl)indenyl)titanium dichloride
1,3-propanediylbis(2-cyclohexyl-4-(4'-methoxyphenyl)indenyl)titanium dichloride
1,3-propanediylbis(2-cyclohexyl-4-(1'-naphthyl)indenyl)titanium dichloride
1,3-propanediylbis(2-cyclohexyl-4-(9'-anthracenyl)indenyl)titanium dichloride
1,3-propanediylbis(2-cyclohexyl-4-(3',5'-di-tert-butylphenyl)indenyl)titanium dichloride
1,3-propanediylbis(2-cyclohexyl-4-(4'-trifluoromethylphenyl)indenyl)titanium dichloride
1,3-propanediylbis(2-methylindenyl)hafnium dichloride
1,3-propanediylbis(2-methyl-4,5-benzindenyl)hafnium dichloride
1,3-propanediylbis(2-methyl-4-phenylindenyl)hafnium dichloride
1,3-propanediylbis(2-methyl-4-(4'-methylphenyl)indenyl)hafnium dichloride
1,3-propanediylbis(2-methyl-4-(4'-ethylphenyl)indenyl)hafnium dichloride
1,3-propanediylbis(2-methyl-4-(4'-propylphenyl)indenyl)hafnium dichloride
1,3-propanediylbis(2-methyl-4-(4'-isopropylphenyl)indenyl)hafnium dichloride
1,3-propanediylbis(2-methyl-4-(4'-tert-butylphenyl)indenyl)hafnium dichloride
1,3-propanediylbis(2-methyl-4-(4'-methoxyphenyl)indenyl)hafnium dichloride
1,3-propanediylbis(2-methyl-4-(1'-naphthyl)indenyl)hafnium dichloride
1,3-propanediylbis(2-methyl-4-(9'-anthracenyl)indenyl)hafnium dichloride
1,3-propanediylbis(2-methyl-4-(3',5'-di-tert-butylphenyl)indenyl)hafnium dichloride
1,3-propanediylbis(2-methyl-4-(4'-trifluoromethylphenyl)indenyl)hafnium dichloride
1,3-propanediylbis(2-ethylindenyl)hafnium dichloride
1,3-propanediylbis(2-ethyl-4,5-benzindenyl)hafnium dichloride
1,3-propanediylbis(2-ethyl-4-phenylindenyl)hafnium dichloride
1,3-propanediylbis(2-ethyl-4-(4'-methylphenyl)indenyl)hafnium dichloride
1,3-propanediylbis(2-ethyl-4-(4'-ethylphenyl)indenyl)hafnium dichloride
1,3-propanediylbis(2-ethyl-4-(4'-propylphenyl)indenyl)hafnium dichloride
1,3-propanediylbis(2-ethyl-4-(4'-isopropylphenyl)indenyl)hafnium dichloride
1,3-propanediylbis(2-ethyl-4-(4'-tert-butylphenyl)indenyl)hafnium dichloride
1,3-propanediylbis(2-ethyl-4-(4'-methoxyphenyl)indenyl)hafnium dichloride
1,3-propanediylbis(2-ethyl-4-(1'-naphthyl)indenyl)hafnium dichloride
1,3-propanediylbis(2-ethyl-4-(9'-anthracenyl)indenyl)hafnium dichloride
1,3-propanediylbis(2-ethyl-4-(3',5'-di-tert-butylphenyl)indenyl)hafnium dichloride
1,3-propanediylbis(2-ethyl-4-(4'-trifluoromethylphenyl)indenyl)hafnium dichloride
1,3-propanediylbis(2-propylindenyl)hafnium dichloride
1,3-propanediylbis(2-propyl-4,5-benzindenyl)hafnium dichloride
1,3-propanediylbis(2-propyl-4-phenylindenyl)hafnium dichloride
1,3-propanediylbis(2-propyl-4-(4'-methylphenyl)indenyl)hafnium dichloride
1,3-propanediylbis(2-propyl-4-(4'-ethylphenyl)indenyl)hafnium dichloride
1,3-propanediylbis(2-propyl-4-(4'-propylphenyl)indenyl)hafnium dichloride
1,3-propanediylbis(2-propyl-4-(4'-isopropylphenyl)indenyl)hafnium dichloride
1,3-propanediylbis(2-propyl-4-(4'-tert-butylphenyl)indenyl)hafnium dichloride
1,3-propanediylbis(2-propyl-4-(4'-methoxyphenyl)indenyl)hafnium dichloride
1,3-propanediylbis(2-propyl-4-(1'-naphthyl)indenyl)hafnium dichloride
1,3-propanediylbis(2-propyl-4-(9'-anthracenyl)indenyl)hafnium dichloride
1,3-propanediylbis(2-propyl-4-(3',5'-di-tert-butylphenyl)indenyl)hafnium dichloride
1,3-propanediylbis(2-propyl-4-(4'-trifluoromethylphenyl)indenyl)hafnium dichloride
1,3-propanediylbis(2-isopropylindenyl)hafnium dichloride
1,3-propanediylbis(2-isopropyl-4,5-benzindenyl)hafnium dichloride
1,3-propanediylbis(2-isopropyl-4-phenylindenyl)hafnium dichloride
1,3-propanediylbis(2-isopropyl-4-(4'-methylphenyl)indenyl)hafnium dichloride
1,3-propanediylbis(2-isopropyl-4-(4'-ethylphenyl)indenyl)hafnium dichloride 1,3-propanediylbis(2-isopropyl-4-(4'-propylphenyl)indenyl)hafnium dichloride
1,3-propanediylbis(2-isopropyl-4-(4'-isopropylphenyl)indenyl)hafnium dichloride
1,3-propanediylbis(2-isopropyl-4-(4'-tert-butylphenyl)indenyl)hafnium dichloride
1,3-propanediylbis(2-isopropyl-4-(4'-methoxyphenyl)indenyl)hafnium dichloride
1,3-propanediylbis(2-isopropyl-4-(1'-naphthyl)indenyl)hafnium dichloride
1,3-propanediylbis(2-isopropyl-4-(9'-anthracenyl)indenyl)hafnium dichloride
1,3-propanediylbis(2-isopropyl-4-(3',5'-di-tert-butylphenyl)indenyl)hafnium dichloride
1,3-propanediylbis(2-isopropyl-4-(4'-trifluoromethylphenyl)indenyl)hafnium dichloride
1,3-propanediylbis(2-isobutylindenyl)hafnium dichloride
1,3-propanediylbis(2-isobutyl-4,5-benzindenyl)hafnium dichloride
1,3-propanediylbis(2-isobutyl-4-phenylindenyl)hafnium dichloride
1,3-propanediylbis(2-isobutyl-4-(4'-methylphenyl)indenyl)hafnium dichloride
1,3-propanediylbis(2-isobutyl-4-(4'-ethylphenyl)indenyl)hafnium dichloride
1,3-propanediylbis(2-isobutyl-4-(4'-propylphenyl)indenyl)hafnium dichloride
1,3-propanediylbis(2-isobutyl-4-(4'-isopropylphenyl)indenyl)hafnium dichloride
1,3-propanediylbis(2-isobutyl-4-(4'-tert-butylphenyl)indenyl)hafnium dichloride
1,3-propanediylbis(2-isobutyl-4-(4'-methoxyphenyl)indenyl)hafnium dichloride
1,3-propanediylbis(2-isobutyl-4-(1'-naphthyl)indenyl)hafnium dichloride
1,3-propanediylbis(2-isobutyl-4-(9'-anthracenyl)indenyl)hafnium dichloride
1,3-propanediylbis(2-isobutyl-4-(3',5'-di-tert-butylphenyl)indenyl)hafnium dichloride
1,3-propanediylbis(2-isobutyl-4-(4'-trifluoromethylphenyl)indenyl)hafnium dichloride
1,3-propanediylbis(2-butylindenyl)hafnium dichloride
1,3-propanediylbis(2-butyl-4,5-benzindenyl)hafnium dichloride
1,3-propanediylbis(2-butyl-4-phenylindenyl)hafnium dichloride
1,3-propanediylbis(2-butyl-4-(4'-methylphenyl)indenyl)hafnium dichloride
1,3-propanediylbis(2-butyl-4-(4'-ethylphenyl)indenyl)hafnium dichloride
1,3-propanediylbis(2-butyl-4-(4'-propylphenyl)indenyl)hafnium dichloride
1,3-propanediylbis(2-butyl-4-(4'-isopropylphenyl)indenyl)hafnium dichloride
1,3-propanediylbis(2-butyl-4-(4'-tert-butylphenyl)indenyl)hafnium dichloride
1,3-propanediylbis(2-butyl-4-(4'-methoxyphenyl)indenyl)hafnium dichloride
1,3-propanediylbis(2-butyl-4-(1'-naphthyl)indenyl)hafnium dichloride
1,3-propanediylbis(2-butyl-4-(9'-anthracenyl)indenyl)hafnium dichloride
1,3-propanediylbis(2-butyl-4-(3',5'-di-tert-butylphenyl)indenyl)hafnium dichloride
1,3-propanediylbis(2-butyl-4-(4'-trifluoromethylphenyl)indenyl)hafnium dichloride
1,3-propanediylbis(2-tert-butylindenyl)hafnium dichloride
1,3-propanediylbis(2-tert-butyl-4,5-benzindenyl)hafnium dichloride
1,3-propanediylbis(2-tert-butyl-4-phenylindenyl)hafnium dichloride
1,3-propanediylbis(2-tert-butyl-4-(4'-methylphenyl)indenyl)hafnium dichloride
1,3-propanediylbis(2-tert-butyl-4-(4'-ethylphenyl)indenyl)hafnium dichloride
1,3-propanediylbis(2-tert-butyl-4-(4'-propylphenyl)indenyl)hafnium dichloride
1,3-propanediylbis(2-tert-butyl-4-(4'-isopropylphenyl)indenyl)hafnium dichloride
1,3-propanediylbis(2-tert-butyl-4-(4'-tert-butylphenyl)indenyl)hafnium dichloride
1,3-propanediylbis(2-tert-butyl-4-(4'-methoxyphenyl)indenyl)hafnium dichloride
1,3-propanediylbis(2-tert-butyl-4-(1'-naphthyl)indenyl)hafnium dichloride
1,3-propanediylbis(2-tert-butyl-4-(9'-anthracenyl)indenyl)hafnium dichloride
1,3-propanediylbis(2-tert-butyl-4-(3',5'-di-tert-butylphenyl)indenyl)hafnium dichloride
1,3-propanediylbis(2-tert-butyl-4-(4'-trifluoromethylphenyl)indenyl)hafnium dichloride
1,3-propanediylbis(2-cyclopentylindenyl)hafnium dichloride
1,3-propanediylbis(2-cyclopentyl-4,5-benzindenyl)hafnium dichloride
1,3-propanediylbis(2-cyclopentyl-4-phenylindenyl)hafnium dichloride
1,3-propanediylbis(2-cyclopentyl-4-(4'-methylphenyl)indenyl)hafnium dichloride
1,3-propanediylbis(2-cyclopentyl-4-(4'-ethylphenyl)indenyl)hafnium dichloride
1,3-propanediylbis(2-cyclopentyl-4-(4'-propylphenyl)indenyl)hafnium dichloride
1,3-propanediylbis(2-cyclopentyl-4-(4'-isopropylphenyl)indenyl)hafnium dichloride
1,3-propanediylbis(2-cyclopentyl-4-(4'-tert-butylphenyl)indenyl)hafnium dichloride
1,3-propanediylbis(2-cyclopentyl-4-(4'-methoxyphenyl)indenyl)hafnium dichloride
1,3-propanediylbis(2-cyclopentyl-4-(1'-naphthyl)indenyl)hafnium dichloride
1,3-propanediylbis(2-cyclopentyl-4-(9'-anthracenyl)indenyl)hafnium dichloride
1,3-propanediylbis(2-cyclopentyl-4-(3',5'-di-tert-butylphenyl)indenyl)hafnium dichloride
1,3-propanediylbis(2-cyclopentyl-4-(4'-trifluoromethylphenyl)indenyl)hafnium dichloride
1,3-propanediylbis(2-cyclohexylindenyl)hafnium dichloride
1,3-propanediylbis(2-cyclohexyl-4,5-benzindenyl)hafnium dichloride
1,3-propanediylbis(2-cyclohexyl-4-phenylindenyl)hafnium dichloride
1,3-propanediylbis(2-cyclohexyl-4-(4'-methylphenyl)indenyl)hafnium dichloride
1,3-propanediylbis(2-cyclohexyl-4-(4'-ethylphenyl)indenyl)hafnium dichloride
1,3-propanediylbis(2-cyclohexyl-4-(4'-propylphenyl)indenyl)hafnium dichloride
1,3-propanediylbis(2-cyclohexyl-4-(4'-isopropylphenyl)indenyl)hafnium dichloride
1,3-propanediylbis(2-cyclohexyl-4-(4'-tert-butylphenyl)indenyl)hafnium dichloride
1,3-propanediylbis(2-cyclohexyl-4-(4'-methoxyphenyl)indenyl)hafnium dichloride 1,3-propanediylbis(2-cyclohexyl-4-(1'-naphthyl)indenyl) hafnium dichloride 1,3-propanediylbis(2-cyclohexyl-4-(9'-anthracenyl)indenyl) hafnium dichloride 1,3-propanediylbis(2-cyclohexyl-4-(3',5'-di-tert-butylphenyl)indenyl)hafnium dichloride 1,3-propanediylbis(2-cyclohexyl-4-(4'-trifluoromethylphenyl)indenyl)hafnium dichloride The metallocenes prepared according to the present invention are highly active catalyst components for olefin polymerization. Depending on the substitution pattern of the ligands, the metallocenes can be obtained as mixtures of isomers. For the polymerization, the metallocenes are preferably used as pure isomers, but the use of the racemate is sufficient in most cases. The metallocenes prepared by the process of the present invention can also be used as catalysts in organic synthesis, in which case the pure enantiomers are preferably used.

The metal complexes of the formula I prepared by the process of the present invention are particularly suitable as constituents of catalyst systems for preparing polyolefins by polymerization of at least one olefin in the presence of a catalyst comprising at least one cocatalyst and at least one metal complex.

The cocatalyst which together with a metal complex of the formula I forms the catalyst system comprises at least one compound such as an aluminoxane or Lewis acid or ionic compound which reacts with a metal complex to convert it into a cationic compound.

Examples of such cocatalysts are described in DE 19962905.

The cocatalyst and/or the metal complex can be in unsupported or supported form. Examples of supported cocatalysts and/or supported metal complexes are described in DE 19962905.

The support component of the catalyst system can be any organic or inorganic, inert solid, in particular a porous support such as talc, inorganic oxides and finely divided polymer powders (e.g. polyolefins). Examples of suitable support materials and methods of application to the support are described in DE 19962905.

For the purposes of the present invention, the term polymerization encompasses both homopolymerization and copolymerization.

Preference is given to polymerizing olefins of the formula $R_m$—CH=CH—$R_n$, where $R_m$ and $R_n$ are identical or different and are each a hydrogen atom or a carbon-containing radical having from 1 to 20 carbon atoms, in particular from 1 to 10 carbon atoms, and $R_m$ and $R_n$ together with the atoms connecting them may form one or more rings. Examples of such olefins are described in DE 19962905.

The polymerization is carried out at from 0 to 300° C., preferably from 50 to 200° C., very particularly preferably 50–80° C. The pressure is from 0.5 to 2000 bar, preferably from 5 to 64 bar.

The polymerization can be carried out in solution, in bulk, in suspension or in the gas phase, continuously or batchwise, in one or more stages. Examples of suitable polymerization processes are described in DE 19962905.

If required, hydrogen is added as molar mass regulator and/or to increase the activity.

The catalyst system can be introduced into the polymerization system in pure form or can, to enable it to be metered more readily, be admixed with inert components such as paraffins, oils or waxes. In addition, an antistatic can be introduced into the polymerization system either together with or separately from the catalyst system used.

In the process of the present invention, the use of a specific bridging reagent of the formula V gives multiply substituted ligand systems of the formula VI in high yields and purities, thus opening up an efficient route to transition metal complexes of the formula I.

The invention is illustrated by the following, nonlimiting examples.

General procedures: Preparation and handling of organometallic compounds were carried out in the absence of air and moisture under argon (Schlenk technique or glove box). All solvents required were purged with argon and dried over molecular sieves before use. 1,2-Bistrifluoromethylsulfonyloxyethane was synthesized as described by Lindner, Ekkehard; Au, Guenter von; Eberle, Hans-Juergen; Chem.Ber.; 114; 2; 1981; 810–813. The preparations of 1,3-bistrifluoromethylsulfonyloxypropane and 1,2-bistrifluoromethylsulfonyloxycyclohexane were carried out analogously. The indenes used were prepared as described in WO 9840331.

EXAMPLE 1

1,2-Bis(2-methyl-4-(4'-tert-butylphenyl)indenyl) ethane

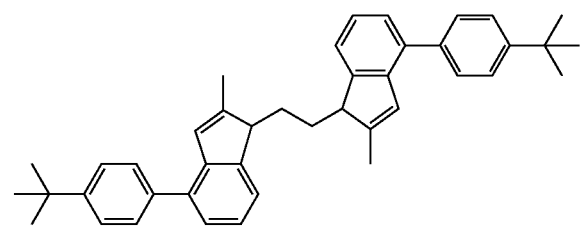

In a 1 l three-neck flask, 39.3 g (150 mmol) of 2-methyl-7-(4'-tert-butylphenyl)indene in 110 ml of tetrahydrofuran were admixed at 0° C. with 60 ml of n-butyllithium (150 mmol, 2.5 M in toluene). The mixture was stirred for another 1 hour at room temperature and the resulting red solution was added dropwise over a period of 30 minutes to a solution of 24.5 g (75 mmol) of 1,2-bistrifluoromethylsulfonyloxyethane in 26 ml of tetrahydrofuran which had been cooled to −40° C. The mixture was stirred for another 1 hour at −20° C. and for 13 hours at room temperature. The solvent was then removed under reduced pressure and the residue was admixed with 150 ml of toluene. The organic phase was washed in succession with 1×100 ml of a saturated NaHCO$_3$ solution, 2×50 ml of a saturated NaHCO$_3$ solution and 2×100 ml of water. The organic phase was dried over magnesium sulfate and the solvent was removed under reduced pressure. The crude product obtained in this way was purified by column chromatography on silica gel, giving the product in a yield of 32 g (58 mmol, 77%) and a purity of >95% (according to GC) in the form of a yellow oil. $^1$H-NMR: δ=7.50–7.16 (m, 14 H, aromat. H), 3.34 (s, 4H, benzyl. H), 2.77 (s, 4H, C2 bridge), 1.94 (s, 6H, CH$_3$), 1.37 (s, 18H, C(CH$_3$)$_3$) ppm.

EXAMPLE 2

1,2-Bis(2-ethyl-4-(4'-tert-butylphenyl)indenyl)ethane

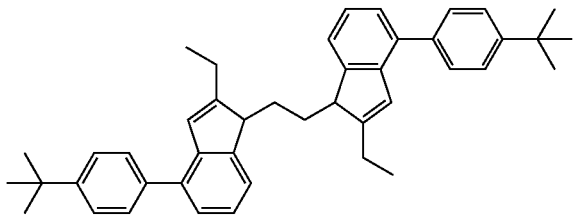

In a 250 ml three-neck flask, 11.1 g (40 mmol) of 2-ethyl-7-(4'-tert-butylphenyl)indene in 30 ml of tetrahydrofuran ere admixed at 0° C. with 16 ml of n-butyllithium (40 mmol, 2.5 M in toluene). The mixture was stirred for another 1 hour at room temperature and the resulting red solution was added dropwise over a period of 30 minutes to a solution of 6.5 g (20 mmol) of 1,2-bistrifluoromethylsulfonyloxyethane in 26 ml of tetrahydrofuran which had been cooled to −40° C. The mixture was stirred for another 1 hour at −20° C. and for 13 hours at room temperature. The solvent was then removed under reduced pressure and the residue was admixed with 150 ml of toluene. The organic phase was washed in succession with 1×100 ml of a saturated $NaHCO_3$ solution, 2×50 ml of a saturated $NaHCO_3$ solution and 2×100 ml of water. The organic phase was dried over magnesium sulfate and the solvent was removed under reduced pressure. The crude product obtained in this way was purified by column chromatography on silica gel, giving the product in a yield of 7.4 g (13 mmol, 64%) and a purity of >95% (according to GC) in the form of a yellow oil. $^1$H-NMR: δ=7.51–7.15 (m, 14 H, aromat. H), 3.32 (s, 4H, benzyl. H), 2.67 (s, 4H, C2 bridge), 1.94 (q, 4H, $CH_2$), 1.37 (s, 18H, $C(CH_3)_3$), 1.07 (t, 6H, $CH_3$) ppm.

EXAMPLE 3

1,2-Bis(2-isopropyl-4-(4'-tert-butylphenyl)indenyl)ethane

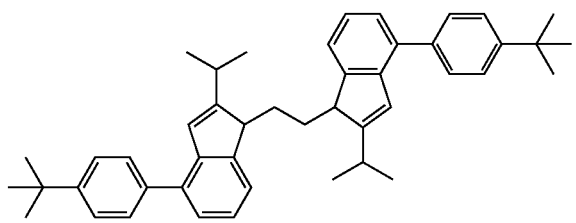

In a 250 ml three-neck flask, 17.4 g (60 mmol) of 2-isopropyl-7-(4'-tert-butylphenyl)indene in 50 ml of tetrahydrofuran were admixed at 0° C. with 24 ml of n-butyllithium (60 mmol, 2.5 M in toluene). The mixture was stirred for another 1 hour at room temperature and the resulting red solution was added dropwise over a period of 30 minutes to a solution of 9.8 g (30 mmol) of 1,2-bistrifluoromethylsulfonyloxyethane in 10 ml of tetrahydrofuran which had been cooled to −40° C. The mixture was stirred for another 1 hour at −20° C. and for 13 hours at room temperature. The solvent was then removed under reduced pressure and the residue was admixed with 150 ml of toluene. The organic phase was washed in succession with 1×100 ml of a saturated $NaHCO_3$ solution, 2×50 ml of a saturated $NaHCO_3$ solution and 2×100 ml of water. The organic phase was dried over magnesium sulfate and the solvent was removed under reduced pressure. The crude product obtained in this way was purified by column chromatography on silica gel, giving the product in a yield of 9 g (15 mmol, 53%) and a purity of >95% (according to GC) in the form of a yellow oil. $^1$H-NMR: δ=7.49–7.13 (m, 14 H, aromat. H), 3.33 (s, 4H, benzyl. H), 2.71 (s, 4H, C2 bridge), 2.52 (m, 2H, isopropyl-H), 1.37 (s, 18H, $C(CH_3)_3$), 1.11 (m, 12H, $CH_3$) ppm.

EXAMPLE 4

1,3-Bis(2-methyl-4-phenylindenyl)propane

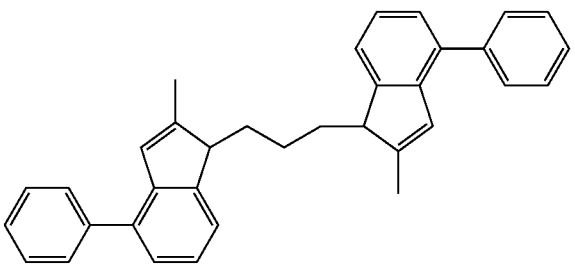

In a 250 ml three-neck flask, 20.6 g (100 mmol) of 2-methyl-7-phenylindene in 100 ml of tetrahydrofuran were admixed at 0° C. with 40 ml of n-butyllithium (100 mmol, 2.5 M in toluene). The mixture was stirred for another 1 hour at room temperature and the resulting red solution was added dropwise over a period of 30 minutes to a solution of 17.1 g (50 mmol) of 1,3-bistrifluoromethylsulfonyloxypropane in 40 ml of tetrahydrofuran which had been cooled to −40° C. The mixture was stirred for another 1 hour at −20° C. and for 13 hours at room temperature. The solvent was then removed under reduced pressure and the residue was admixed with 150 ml of toluene. The organic phase was washed in succession with 1×100 ml of a saturated $NaHCO_3$ solution, 2×50 ml of a saturated $NaHCO_3$ solution and 2×100 ml of water. The organic phase was dried over magnesium sulfate and the solvent was removed under reduced pressure. The crude product obtained in this way was purified by column chromatography on silica gel, giving the product in a yield of 37g (81 mmol, 81% and a purity of >95% (according to GC) in the form of a yellow oil. $^1$H-NMR: δ=7.48–7.08 (m, 16 H, aromat. H), 3.22 (s, 4H, benzyl. H), 1.96 (s, 4H, $CH_2$), 1.71 (s, 6H, $CH_3$), 1.37 (s, 2H, $CH_2$) ppm.

EXAMPLE 5

E-1,2-Bis(2-propyl-4-phenylindenyl)cyclohexane

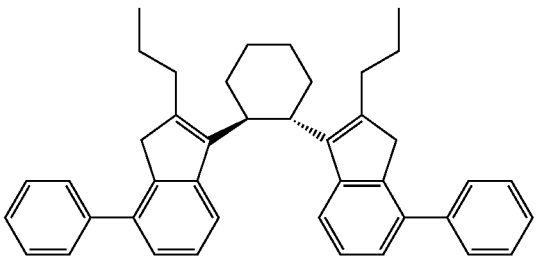

In a 250 ml three-neck flask, 23.4 g (100 mmol) of 2-n-propyl-7-phenylindene in 100 ml of tetrahydrofuran were admixed at 0° C. with 40 ml of n-butyllithium (100 mmol, 2.5 M in toluene). The mixture was stirred for another 1 hour at room temperature and the resulting red solution was added dropwise over a period of 30 minutes to a solution of 19.0 g (50 mmol) of 1,2-bistrifluoromethylsulfonyloxycyclohexane in 40 ml of tetrahydrofuran which had been cooled to −40° C. The mixture was stirred for another 1 hour at −20° C. and for 13 hours at room temperature. The solvent was then removed under reduced pressure and the residue was admixed with 150 ml of toluene. The organic phase was washed in succession with 1×100 ml of a saturated NaHCO$_3$ solution, 2×50 ml of a saturated NaHCO$_3$ solution and 2×100 ml of water. The organic phase was dried over magnesium sulfate and the solvent was removed under reduced pressure. The crude product obtained in this way was purified by column chromatography on silica gel, giving the product in a yield of 43 g (79 mmol, 79%) and a purity of >95% (according to GC) in the form of a yellow oil. $^1$H-NMR: δ=7.50–7.06 (m, 16 H, aromat. H), 3.33 (s, 4H, benzyl. H), 1.94–0.96 (m, 24H, CH, CH$_2$, CH$_3$) ppm.

EXAMPLE 6

1,2-Ethanediylbis(2-methyl-4-(4'-tert-butylphenyl) indenyl)zirconium dichloride

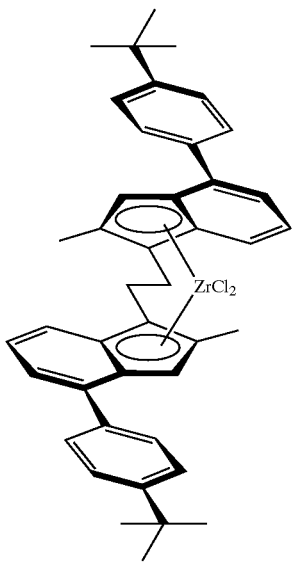

9.1 g (16.5 mmol) of 1,2-bis(2-methyl-4-(4'-tert-butylphenyl)indenyl)ethane and 230 ml of diethyl ether were placed in a 500 ml three-neck flask. The suspension was admixed at room temperature with 20.7 ml (33.1 mmol, 1.6 M in hexane) of n-BuLi.

The now yellow suspension was stirred at room temperature for 12 hours. 5.3 g (16.5 mmol) of zirconium tetrachloride•dimethoxyethane adduct were then added at 0° C. The suspension was stirred at RT for another 12 hours. The yellow solid was isolated by filtration on a G3 frit and washed with 20 ml of diethyl ether. The LiCl-containing crude complex (quant.) was stirred with 310 ml of toluene at 80° C. in a 1 l flask and was then filtered through toluene-moist Celite. The Celite was washed with another 150 ml of toluene which had been heated to 80° C. The filtrate was evaporated to 20 ml and stored at 4° C., resulting in the complex crystallizing as yellow needles. Filtration gave 3.4 g (4.8 mmol, 29%, r/m>4:1) of the yellow complex. $^1$H-NMR: δ=7.75–6.97 (m, 14 H, aromat. H), 6.54 (s, 2H, Cp-Ind-H), 4.10, 3.60 (2×m, 4H, CH$_2$CH$_2$), 2.12 (s, 6H, CH$_3$), 1.31 (s, 18H, tert-butyl) ppm.

EXAMPLE 7

1,2-Ethanediylbis(2-ethyl-4-(4'-tert-butylphenyl) indenyl)zirconium dichloride

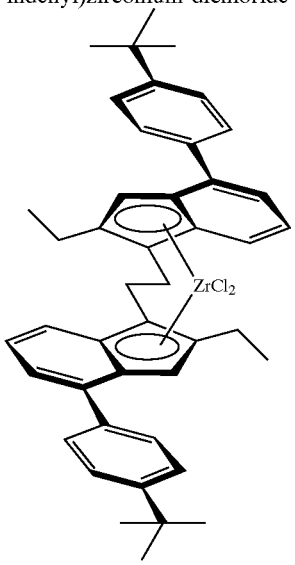

7.4 g (13.0 mmol) of 1,2-bis(2-ethyl-4-(4'-tert-butylphenyl)indenyl)ethane and 200 ml of diethyl ether were placed in a 500 ml three-neck flask. The suspension was admixed at room temperature with 16.3 ml (26 mmol, 1.6 M in hexane) of n-BuLi.

The now yellow suspension was stirred at room temperature for 12 hours. 4.2 g (13.0 mmol) of zirconium tetrachloride•dimethoxyethane adduct were then added at 0° C. The suspension was stirred at RT for another 12 hours. The yellow solid was isolated by filtration on a G3 frit and washed with 20 ml of diethyl ether. The LiCl-containing crude complex (quant.) was stirred with 240 ml of toluene at 80° C. in a 1 l flask and was then filtered through toluene-moist Celite. The Celite was washed with another 100 ml of toluene which had been heated to 80° C. The filtrate was evaporated to 20 ml and stored at 4° C., resulting in the complex crystallizing as yellow needles. Filtration gave 3.3 g (4.5 mmol, 34%, r/m>7:1) of the yellow complex. $^1$H-NMR: δ=7.70–6.92 (m, 14 H, aromat. H), 6.52 (s, 2H, Cp-Ind-H), 4.11, 3.62 (2×m, 4H, CH$_2$CH$_2$), 2.86 (m, 4H, CH$_2$), 1.32 (s, 18H, tert-butyl), 0.88 (m, 6H, CH$_3$) ppm.

EXAMPLE 8

1,2-Ethanediylbis(2-isopropyl-4-(4'-tert-butylphenyl) indenyl)zirconium dichloride

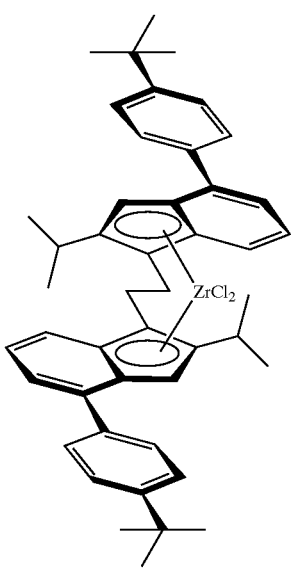

9.0 g (15.0 mmol) of 1,2-bis(2-isopropyl-4-(4'-tert-butylphenyl)indenyl)ethane and 210 ml of diethyl ether were placed in a 500 ml three-neck flask. The suspension was admixed at room temperature with 18.8 ml (30 mmol, 1.6 M in hexane) of n-BuLi.

The now yellow suspension was stirred at room temperature for 12 hours. 4.8 g (15 mmol) of zirconium tetrachloride•dimethoxyethane adduct were then added at 0° C. The suspension was stirred at RT for another 12 hours. The yellow solid was isolated by filtration on a G3 frit and washed with 20 ml of diethyl ether. The LiCl-containing crude complex (quant.) was stirred with 220 ml of toluene at 80° C. in a 1 l flask and was then filtered through toluene-moist Celite. The Celite was washed with another 90 ml of toluene which had been heated to 80° C. The filtrate was evaporated to 20 ml and stored at 40° C., resulting in the complex crystallizing as yellow needles. Filtration gave 3.7 g (4.8 mmol, 32%, r/m>5:1) of the yellow complex. $^1$H-NMR: δ=7.74–6.90 (m, 14 H, aromat. H), 6.55 (s, 2H, Cp-Ind-H), 4.12, 3.63 (2×m, 4H, CH$_2$CH$_2$), 2.97 (m, 2H, CH), 1.31 (s, 18H, tert-butyl), 0.80 (m, 12H, CH$_3$) ppm.

EXAMPLE 9

1,3-Propanediylbis(2-methyl-4-phenyl-indenyl) zirconium dichloride

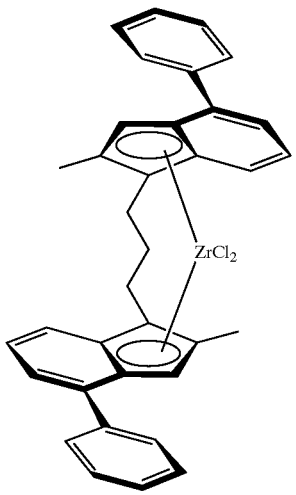

7.6 g (15.0 mmol) of 1,3-bis(2-methyl-4-phenylindenyl)propane and 210 ml of diethyl ether were placed in a 500 ml three-neck flask. The suspension was admixed at room temperature with 18.8 ml (30 mmol, 1.6 M in hexane) of n-BuLi.

The now yellow suspension was stirred at room temperature for 12 hours. 4.8 g (15 mmol) of zirconium tetrachloride•dimethoxyethane adduct were then added at 0° C. The suspension was stirred at RT for another 12 hours. The yellow solid was isolated by filtration on a G3 frit and washed with 20 ml of diethyl ether. The LiCl-containing crude complex (quant.) was stirred with 210 ml of toluene at 80° C. in a 1 l flask and was then filtered through toluene-moist Celite. The Celite was washed with another 100 ml of toluene which had been heated to 80° C. The filtrate was evaporated to 20 ml and stored at 40° C., resulting in the complex crystallizing as yellow needles. Filtration gave 3.9 g (5.8 mmol, 38%, r/m>3:1) of the yellow complex. $^1$H-NMR: δ=7.69–6.87 (m, 16 H, aromat. H), 6.43 (s, 2H, Cp-Ind-H), 4.15, 3.73 (2×m, 6H, CH$_2$CH$_2$), 2.11 (s, 6H, CH$_3$) ppm.

EXAMPLE 10

1,2–Cyclohexanediylbis(2-propyl-4-phenyl)indenyl) zirconium dichloride

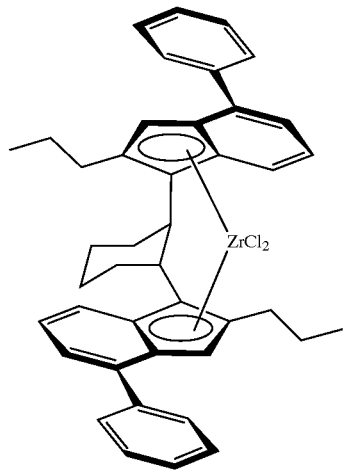

8.2 g (15.0 mmol) of 1,2-bis(2-methyl-4-phenylindenyl)cyclohexane and 210 ml of diethyl ether were placed in a 500 ml three-neck flask. The suspension was admixed at room temperature with 18.8 ml (30 mmol, 1.6 M in hexane) of n-BuLi.

The now yellow suspension was stirred at room temperature for 12 hours. 4.8 g (15 mmol) of zirconium tetrachloride-dimethoxyethane adduct were then added at 0° C. The suspension was stirred at RT for another 12 hours. The yellow solid was isolated by filtration on a G3 frit and washed with 20 ml of diethyl ether. The LiCl-containing crude complex (quant.) was stirred with 180 ml of toluene at 80° C. in a 1 l flask and was then filtered through toluene-moist Celite. The Celite was washed with another 80 ml of toluene which had been heated to 80° C. The filtrate was evaporated to 20 ml and stored at 4° C., resulting in the complex crystallizing as yellow needles. Filtration gave 3.3 g (4.7 mmol, 31%, r/m>4:1) of the yellow complex. $^1$H-NMR: δ=7.74–6.89 (m, 16 H, aromat. H), 6.47 (s, 2H, Cp-Ind-H), 4.01, 3.52 (2×m, 2H, CHCH), 2.96 (m, 4H, CH$_2$), 1.33–0.88 (m, 18H, CH$_2$, CH$_3$, Cy-CH$_2$) ppm.

We claim:

1. A process for preparing compounds of the formula I:

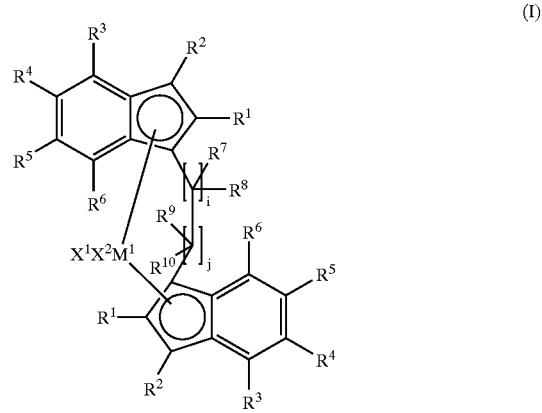

(I)

where

M$^1$ is Ti, Zr or Hf, $R^1$ are identical or different and are each hydrogen or a $C_1$–$C_{20}$ group, and $R^2$ are identical or different and are each hydrogen or a $C_1$–$C_{20}$ group, where $R^1$ together with $R^2$ may also form a monocyclic or polycyclic ring system, and $R^3$ are identical or different and are each a hydrogen atom or a $C_6$–$C_{18}$-aryl group which may be substituted, $C_5$–$C_{18}$-heteroaryl, $C_7$–$C_{20}$-arylalkyl, $C_7$–$C_{20}$-alkylaryl, fluorinated $C_6$–$C_{18}$-aryl, fluorinated $C_7$–$C_{20}$-arylalkyl or fluorinated $C_7$–$C_{20}$-alkylaryl, and two radicals $R^3$ and $R^4$ may form a monocyclic or polycyclic ring system, $R^4$ are identical or different and are each a hydrogen atom or together with $R^3$ form a monocyclic or polycyclic ring system, $R^5$, $R^6$ are identical or different and are each a hydrogen atom or a $C_1$–$C_{20}$ group, $R^7$, $R^8$, $R^9$, $R^{10}$ are identical or different and are each a hydrogen atom or a $C_1$–$C_{20}$ group, and may, among one another, form a monocyclic or bicyclic ring system, i is from 1 to 10 and j is from 1 to 10 and $X^1$, $X^2$ may be identical or different and are halogen atoms, alkyl groups or substituted or unsubstituted phenoxides or $X^1$ together with one or more radicals $X^1$ or $X^2$ forms a monocyclic or polycyclic ring system, comprising the following steps:

A) reacting a compound of the formula II

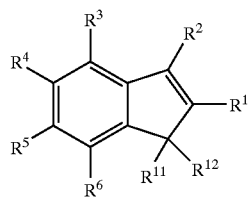

(II)

where $R^1$, $R^2$, $R^3$, $R^4$, $R^5$ and $R^6$ are as defined above and $R^{11}$ is a hydrogen atom and $R^{12}$ is hydrogen or a group which can be replaced by a metal, with a compound of the formula III $M^2R^{13}$ (III)

where $M^2$ is lithium and $R^{13}$ is a hydrogen atom or a $C_1$–$C_{20}$ group to form a compound of the formula IV

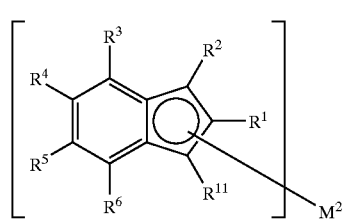

(IV)

where $R^1$, $R^2$, $R^3$, $R^4$, $R^5$, $R^6$, $R^{11}$ are as defined above and $M^2$ is as defined above B) reacting the compound of the formula IV obtained from step A) with a compound of the formula V

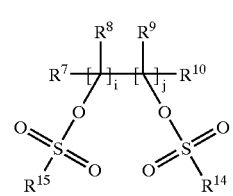

(V)

where $R^7$, $R^8$, $R^9$ and $R^{10}$ are as defined above and $R^{14}$, $R^{15}$ are identical and are trifluoromethyl and i is from 1 to 10 and j is from 1 to 10, to form a compound of the formula VI

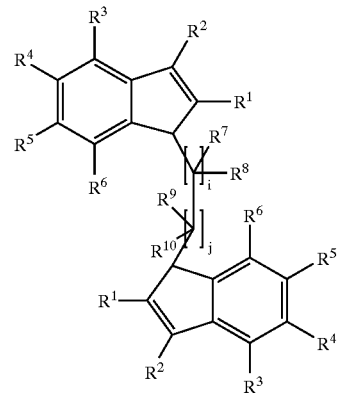

(VI)

where $R^1$, $R^2$, $R^3$, $R^4$, $R^5$, $R^6$, $R^7$, $R^8$, $R^9$, $R^{10}$ are as defined above and i and j are as defined above, C) reacting the compound of the formula VI obtained from step B) with a compound of the formula III as described in step A) to form a compound of the formula VII

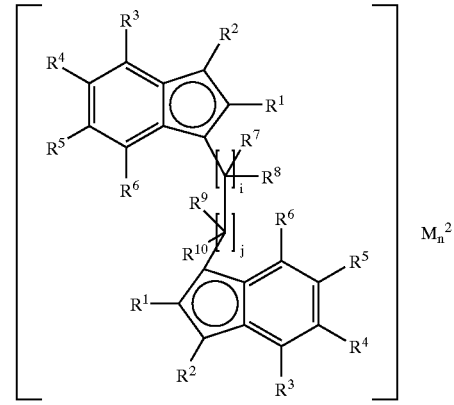

(VII)

where $R^1$, $R^2$, $R^3$, $R^4$, $R^5$, $R^6$, $R^7$, $R^8$, $R^9$, $R^{10}$ and $R^{11}$ are as defined above and M² is as defined above and n is 2 and i and j are as defined above, and A) reacting the compound of the formula VII obtained from step C) with a compound of the formula VIII

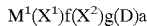
M¹(X¹)f(X²)g(D)a where

M¹ is an element of transition groups I to VIII of the Periodic Table of the Elements and D is a donor solvent containing at least one oxygen atom and/or sulfur atom, and X¹ and X² are identical or different and are as defined above, and f is from 0 to 4, and g is from 0 to 4 and the sum of f+g corresponds to the oxidation state of the metal ion, and a is from 1 to 100, to give the target compound of the formula I.

2. A process as claimed in claim 1, wherein

M¹ is zirconium,

R¹ are identical or different and are each hydrogen, $C_1$–$C_{18}$-alkyl, $C_2$–$C_{10}$-alkenyl, $C_3$–$C_{15}$-alkylalkenyl, $C_6$–$C_{18}$-aryl, $C_4$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, and R² are identical or different and are each hydrogen, $C_1$–$C_{18}$-alkyl, $C_2$–$C_{10}$-alkenyl, $C_3$–$C_{15}$-alkylalkenyl, $C_6$–$C_{18}$-aryl, $C_4$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, where R¹ together with R² may also form a monocyclic or polycyclic ring system, and R³ are identical or different and are each a hydrogen atom or a $C_6$–$C_{18}$-aryl group which may be substituted, $C_5$–$C_{18}$-heteroaryl, $C_7$–$C_{20}$-arylalkyl, $C_7$–$C_{20}$-alkylaryl, fluorinated $C_6$–$C_{18}$-aryl, fluorinated $C_7$–$C_{20}$-arylalkyl or fluorinated $C_7$–$C_{20}$-alkylaryl, and two radicals R³ and R⁴ may form a monocyclic or polycyclic ring system, R⁵, R⁶ are identical or different and are each a hydrogen atom, $C_2$–$C_{10}$-alkenyl, $C_3$–$C_{15}$-alkylalkenyl, $C_6$–$C_{18}$-aryl, $C_4$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, R⁷, R⁸, R⁹, R¹⁰ are identical or different and are each a hydrogen atom, $C_1$–$C_{10}$-alkyl, $C_2$–$C_{10}$-alkenyl, $C_3$–$C_{15}$-alkylalkenyl, $C_6$–$C_{18}$-aryl, $C_4$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, and may, among one another, form a monocyclic or bicyclic ring system, i is from 1 to 3 and j is from 1 to 3 and R¹² is hydrogen, chlorine, bromine or iodine, M² is lithium, and R¹³ is a hydrogen atom, $C_1$–$C_{18}$-alkyl, $C_2$–$C_{10}$-alkenyl, $C_3$–$C_{15}$-alkylalkenyl, $C_6$–$C_{18}$-aryl, $C_5$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, R¹⁴, R¹⁵ are identical and are trifluoromethyl and n is 2 and D is a donor solvent containing at least one oxygen atom and X¹ and X² are identical or different and are each halogen or a phenoxide, and f is from 1 to 4, and g is from 1 to 4 and the sum f+g corresponds to the oxidation state of the metal ion, and a is from 1 to 10.

3. A process as claimed in claim 1, wherein D is an ether, a cyclic ether or an acetal.

4. A process as claimed in claim 3, wherein D is tetrahydrofuran, tetrahydropyran, diethyl ether, dimethoxymethane, diethoxymethane, dipropoxymethane, 1,2-dimethoxyethane, 1,2-diethoxyethane, 1,2-dipropoxyethane, 1,3-dimethoxypropane; 1,3-diethoxypropane, 1,3-dipropoxypropane, 1,2-dimethoxybenzene, 1,2-diethoxybenzene and/or 1,2-dipropoxybenzene.

5. A process as claimed in claim 1, wherein R¹ are all identical and R² are all identical and are each a $C_1$–$C_{20}$ group, where R¹ together with R² may also form a monocyclic or polycyclic ring system.

6. A process as claimed in claim 5, wherein the radicals R¹ are identical and are each $C_1$–$C_{18}$-alkyl, $C_2$–$C_{10}$-alkenyl, $C_3$–$C_{15}$-alkylalkenyl, $C_6$–$C_{18}$-aryl, $C_4$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl and the radicals R² are identical and are each $C_1$–$C_{18}$-alkyl, $C_2$–$C_{10}$-alkenyl, $C_3$–$C_{15}$-alkylalkenyl, $C_6$–$C_{18}$-aryl, $C_4$–$C_{18}$-heteroaryl, $C_7$–$C_{20}$-arylalkyl, $C_7$–$C_{20}$-alkylaryl, fluorinated $C_1$–$C_{12}$-alkyl, fluorinated $C_6$–$C_{18}$-aryl, fluorinated $C_7$–$C_{20}$-arylalkyl or fluorinated $C_7$–$C_{20}$-alkylaryl, where R¹ together with R² may also form a monocyclic or polycyclic ring system.

* * * * *